United States Patent [19]

Sliwa, Jr. et al.

[11] Patent Number: 5,465,724
[45] Date of Patent: Nov. 14, 1995

[54] COMPACT ROTATIONALLY STEERABLE ULTRASOUND TRANSDUCER

[75] Inventors: John W. Sliwa, Jr., Palo Alto; Thomas G. Cooper, Menlo Park; Sevig Ayter, Cupertino, all of Calif.

[73] Assignee: Acuson Corporation, Mountain View, Calif.

[21] Appl. No.: 69,092

[22] Filed: May 28, 1993

[51] Int. Cl.6 .................................................. A61B 8/00
[52] U.S. Cl. ............................................. 128/662.03
[58] Field of Search ............. 128/660.08, 660.09, 128/660.10, 661.01, 661.07, 662.06, 662.03, 898; 73/633

[56] References Cited

U.S. PATENT DOCUMENTS

| | | | |
|---|---|---|---|
| 3,387,604 | 6/1968 | Erikson | 73/625 |
| 3,744,479 | 7/1973 | Stein et al. | 128/660.04 |
| 3,955,561 | 5/1976 | Eggleton | 128/660.10 |
| 3,958,559 | 5/1976 | Glenn et al. | 128/663.01 |
| 3,964,296 | 6/1976 | Matzuk | 73/607 |
| 4,044,594 | 8/1977 | Owens et al. | 73/621 |
| 4,092,867 | 6/1978 | Matzuk | 73/609 |
| 4,109,642 | 8/1978 | Reid et al. | 128/662.01 |

(List continued on next page.)

FOREIGN PATENT DOCUMENTS

| | | | |
|---|---|---|---|
| 509297A1 | 3/1992 | European Pat. Off. | 73/625 |
| 0514584 | 11/1992 | European Pat. Off. . | |
| WO9202178 | 2/1992 | WIPO . | |

OTHER PUBLICATIONS

S. Segaw et al., *Ultrasonic Piezomotor Equipped with a Piezoelectric Rotary Encoder*, 1990 Ultrasonics Symposium (IEEE) 1205–1209.

S. Segawa, *Ultrasonic Piezomotor with a Piezoelectric Angle Detector*, NEC Res. & Develop., vol. 33, No. 1, pp. 55–63, Jan. 1992.

K. Uchino, *Piezoelectric and Electrostrictive Actuators*, pp. 610–618 (IEEE 1986).

K. Hisanaga et al., *A New Transesophageal Real–Time Linear Scanner and Initial Clinical Results*, American Institute of Ultrasound in Medicine, vol. 1, p. 112 (Oct. 1978).

K. Hisanaga et al., *A New Trans–Digestive–Tract Scanner with a Gastro–Fiber–Scope*, American Institute of Ultrasound in Medicine, vol. 1, p. 108 (Oct. 1978).

K. Uchino, *Electrostrictive Actuators: Materials and Applications*, Ceramic Bulletin, vol. 65, No. 4, pp. 647–652 (1986).

M. Fleischer et al., *Novel Ultrasonic Motors with Mono– and Bimodal Drives*, Sensors and Actuators, pp. 357–361, A21–A23 (1990).

A. Yerofeyev, *Multidimensional Control Methods for Piezoelectric Motors*, Vibration Engineering, 3:7–12 (1989).

M. Fleischer et al., *Ultrasonic Piezomotor with Longitudinally Oscillating Amplitude–Transforming Resonator*, IEEE Trans. on Ultrasonics, Ferroelectrics, and Frequency Control, vol. 36, No. 6, pp. 607–613 (Nov. 1989).

P. Hanrath et al., *Transesophageal Horizontal and Sagittal Imaging of the Heart with a Phased Array System Initial Clinical Results*, pp. 280–288 (1982).

*Primary Examiner*—George Manuel
*Attorney, Agent, or Firm*—Willian Brinks Hofer Gilson & Lione

[57] ABSTRACT

According to the present invention, an ultrasonic probe for use with a remote ultrasonic imaging system is provided, having a multielement transducer with an upper surface and a lower surface. An ultrasonically attenuative backing material adjoins the lower surface of the multielement transducer. The attenuative backing material is disposed within a container. A circular track is mounted to the container, and a flexible assembly and a carrier band are attached to the container. The carrier band may be operable to rotate the multielement transducer about an axis defined by the circular track. Alternatively, the circular track may be operable to rotate the multielement transducer. Additionally, a method of forming near real-time images of an object in a plane that is oblique to the axis of rotation of the multielement transducer is provided.

91 Claims, 9 Drawing Sheets

U.S. PATENT DOCUMENTS

| | | | |
|---|---|---|---|
| 4,149,419 | 4/1979 | Connell, Jr. et al. | 73/621 |
| 4,177,679 | 12/1979 | Soldner | 73/625 |
| 4,184,094 | 1/1980 | Kopel | 310/335 |
| 4,205,686 | 6/1980 | Harris et al. | 128/662.03 |
| 4,228,687 | 10/1980 | Fraser | 73/626 |
| 4,231,373 | 11/1980 | Waxman et al. | 128/660.10 |
| 4,232,556 | 11/1980 | Cole | 73/626 |
| 4,244,227 | 1/1981 | Rudolph et al. | 73/621 |
| 4,245,511 | 1/1981 | Soldner | 73/625 |
| 4,269,066 | 5/1981 | Fischer | 73/639 |
| 4,272,991 | 6/1981 | Cribbs | 73/621 |
| 4,273,111 | 6/1981 | Tsukaya | 128/6 |
| 4,296,349 | 10/1981 | Nakanishi et al. | 310/335 |
| 4,315,435 | 2/1982 | Proudian | 73/628 |
| 4,341,120 | 7/1982 | Anderson | 73/618 |
| 4,344,159 | 8/1982 | Ballinger | 367/87 |
| 4,374,525 | 2/1983 | Baba | 128/662.06 |
| 4,375,818 | 3/1983 | Suwaki et al. | 128/662.06 |
| 4,383,447 | 5/1983 | Kretz | 73/626 |
| 4,385,255 | 5/1983 | Yamaguchi et al. | 310/335 |
| 4,387,720 | 6/1983 | Miller | 128/663.01 |
| 4,398,422 | 8/1983 | Haerten | 73/626 |
| 4,398,425 | 8/1983 | Matzuk | 73/633 |
| 4,399,703 | 8/1983 | Matzuk | 73/621 |
| 4,402,223 | 9/1983 | Naumann, Jr. et al. | 73/625 |
| 4,410,826 | 10/1983 | Waxman et al. | 310/335 |
| 4,419,987 | 12/1983 | Ogiu | 128/4 |
| 4,426,886 | 1/1984 | Finsterwald et al. | 73/633 |
| 4,444,197 | 4/1984 | Koyano et al. | 128/660.07 |
| 4,453,409 | 6/1984 | Naumann, Jr. et al. | 73/639 |
| 4,454,763 | 6/1984 | Mahler | 73/639 |
| 4,455,872 | 6/1984 | Kossoff et al. | 73/618 |
| 4,462,408 | 7/1984 | Silverstein et al. | 128/62.06 |
| 4,466,444 | 8/1984 | Baba | 128/662.06 |
| 4,479,388 | 10/1984 | Matzuk | 73/634 |
| 4,501,277 | 2/1985 | Hongo | 128/660.05 |
| 4,503,861 | 3/1985 | Entrekin | 128/662.04 |
| 4,509,368 | 4/1985 | Whiting et al. | 73/624 |
| 4,517,840 | 5/1985 | Thompso et al. | 73/644 |
| 4,524,622 | 6/1985 | Suzuki et al. | 73/620 |
| 4,530,362 | 7/1985 | Hetz | 128/660.10 |
| 4,541,435 | 9/1985 | Saito et al. | 73/626 |
| 4,541,436 | 9/1985 | Hassler et al. | 128/660.07 |
| 4,543,960 | 10/1985 | Harui et al. | 128/662.06 |
| 4,550,608 | 11/1985 | Carnes et al. | 73/633 |
| 4,567,895 | 2/1986 | Putzke | 128/660.1 |
| 4,572,200 | 2/1986 | Schroeder et al. | 128/660.1 |
| 4,572,201 | 2/1986 | Kondo et al. | 128/662.06 |
| 4,593,314 | 6/1986 | Siler | 348/163 |
| 4,601,292 | 7/1986 | Fidel et al. | 128/662.04 |
| 4,622,501 | 11/1986 | Eventoff et al. | 318/627 |
| 4,625,731 | 12/1986 | Quedens et al. | 128/660.07 |
| 4,649,926 | 3/1987 | Abbott et al. | 128/660.09 |
| 4,718,421 | 1/1988 | Rohwedder et al. | 310/325 |
| 4,722,225 | 2/1988 | Hardy et al. | 73/622 |
| 4,722,345 | 2/1988 | Ueno et al. | 128/660.09 |
| 4,735,211 | 4/1988 | Takasugi | 128/660.07 |
| 4,756,313 | 7/1988 | Terwilliger | 128/660.1 |
| 4,757,818 | 7/1988 | Angelsen | 128/660.1 |
| 4,773,426 | 9/1988 | Molnar et al. | 128/660.1 |
| 4,785,819 | 11/1988 | Pearce | 128/660.1 |
| 4,787,247 | 11/1988 | Wuchinich et al. | 73/620 |
| 4,802,458 | 2/1989 | Finsterwald et al. | 128/661.08 |
| 4,802,487 | 2/1989 | Martin et al. | 128/662.06 |
| 4,817,616 | 4/1989 | Goldstein | 128/662.06 |
| 4,841,979 | 6/1989 | Dow et al. | 128/660.01 |
| 4,850,362 | 7/1989 | Rello et al. | 128/660.05 |
| 4,858,613 | 8/1989 | Fry et al. | 128/660.03 |
| 4,869,257 | 9/1989 | Molnar et al. | 128/660.1 |
| 4,869,258 | 9/1989 | Hetz | 128/660.1 |
| 4,880,009 | 11/1989 | Yanagawa | 128/660.09 |
| 4,880,011 | 11/1989 | Imade et al. | 128/662.06 |
| 4,880,012 | 11/1989 | Sato | 128/663.01 |
| 4,893,628 | 1/1990 | Angelsen | 128/660.05 |
| 4,901,729 | 2/1990 | Saitoh et al. | 128/662.03 |
| 4,913,158 | 4/1990 | Kikuchi et al. | 128/660.1 |
| 4,928,699 | 5/1990 | Sasai | 128/662.06 |
| 4,930,515 | 6/1990 | Terwilliger | 128/662.06 |
| 4,932,414 | 6/1990 | Coleman et al. | 128/660.09 |
| 4,936,307 | 6/1990 | Saito et al. | 128/662.06 |
| 4,977,898 | 12/1990 | Schwarzschild et al. | 128/662.06 |
| 4,982,724 | 1/1991 | Saito et al. | 128/6 |
| 4,989,582 | 2/1991 | Sakiyama et al. | 128/6 |
| 4,993,416 | 2/1991 | Ophir | 73/599 |
| 4,996,974 | 3/1991 | Ciarlei | 128/4 |
| 5,020,539 | 6/1991 | Yokoi et al. | 128/4 |
| 5,048,529 | 9/1991 | Blumenthal | 73/633 |
| 5,054,492 | 10/1991 | Scribner et al. | 128/662.06 |
| 5,070,879 | 12/1991 | Herres | 128/660.08 |
| 5,085,221 | 2/1992 | Ingebrigtsen et al. | 73/633 |
| 5,088,495 | 2/1992 | Miyagawa | 73/633 |
| 5,097,838 | 3/1992 | Hirooka et al. | 128/4 |
| 5,099,850 | 3/1992 | Matsui et al. | 128/4 |
| 5,107,844 | 4/1992 | Kami et al. | 128/662.06 |
| 5,127,410 | 7/1992 | King et al. | 73/625 |
| 5,131,396 | 7/1992 | Ishiguro et al. | 128/662.03 |
| 5,131,397 | 7/1992 | Crowley | 128/662.06 |
| 5,156,155 | 10/1992 | King | 128/662.06 |
| 5,158,087 | 10/1992 | Gatzke | 128/662.03 |
| 5,159,931 | 11/1992 | Pini | 73/626 |
| 5,165,414 | 11/1992 | Larson, III | 73/620 |
| 5,167,234 | 12/1992 | Watanabe et al. | 73/606 |
| 5,168,878 | 12/1992 | Takano | 128/662.06 |
| 5,170,793 | 12/1992 | Takano et al. | 128/662.06 |
| 5,174,155 | 12/1992 | Sugimoto | 73/622 |
| 5,176,142 | 1/1993 | Mason | 128/662.06 |
| 5,178,150 | 1/1993 | Silverstein et al. | 128/662.06 |
| 5,181,514 | 1/1993 | Solomon et al. | 128/4 |
| 5,191,890 | 3/1993 | Hileman | 128/662.06 |
| 5,199,437 | 4/1993 | Langberg | 128/662.06 |
| 5,207,225 | 5/1993 | Oaks et al. | 128/660.1 |
| 5,211,176 | 5/1993 | Ishiguro et al. | 128/662.06 |
| 5,215,092 | 6/1993 | Wray | 128/4 |
| 5,226,422 | 7/1993 | McKeighen et al. | |
| 5,297,553 | 3/1994 | Sliwa, Jr. et al. | |
| 5,305,755 | 4/1994 | Nakao | |
| 5,320,104 | 6/1994 | Fearnside et al. | 128/662.06 |

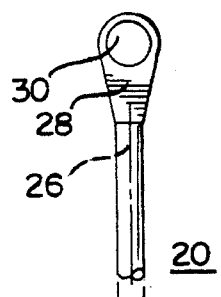
FIG. 1
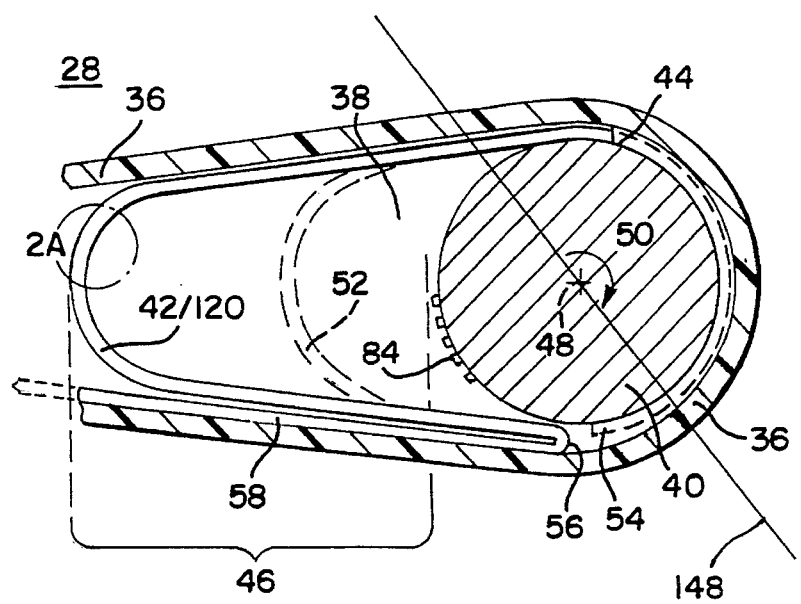
FIG. 2
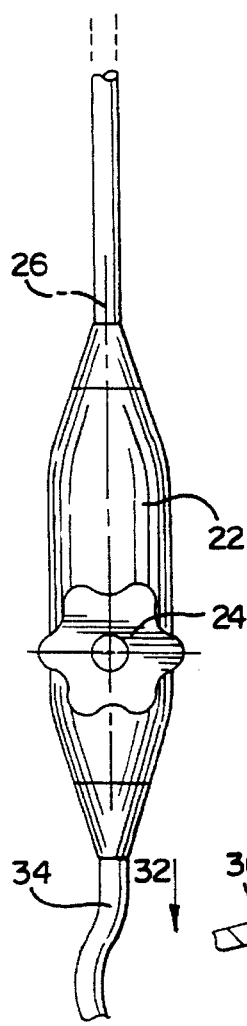
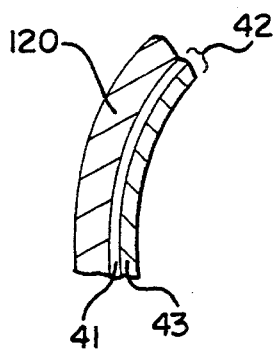
FIG. 2A
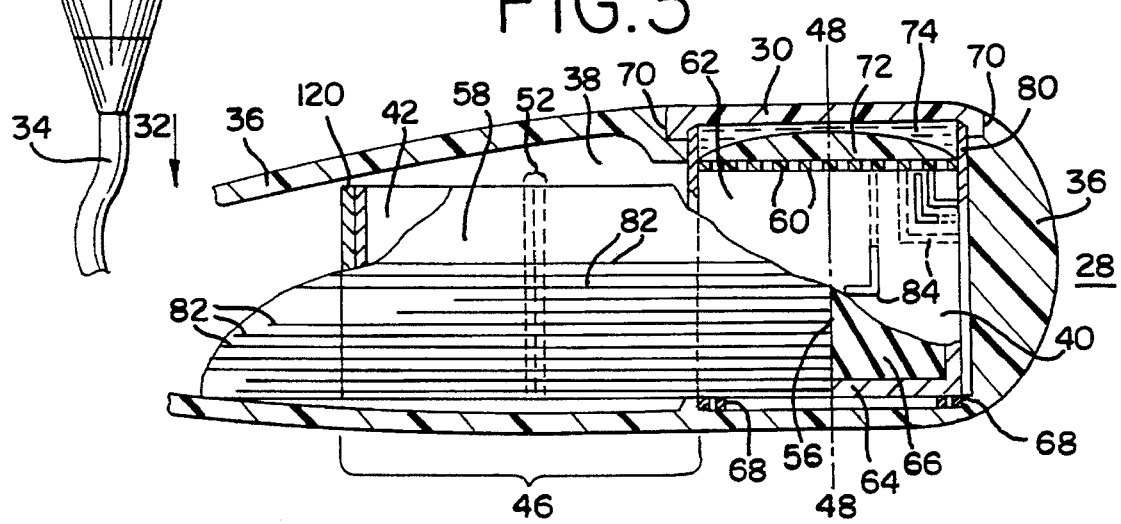
FIG. 3

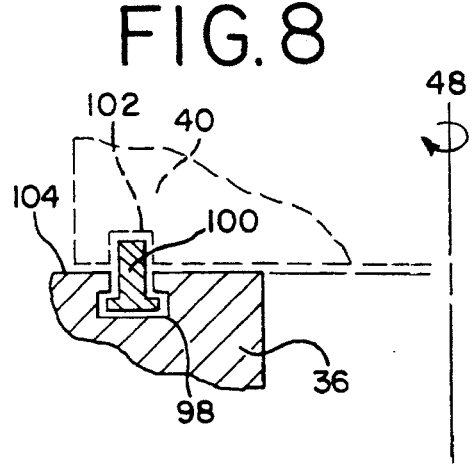
FIG. 8
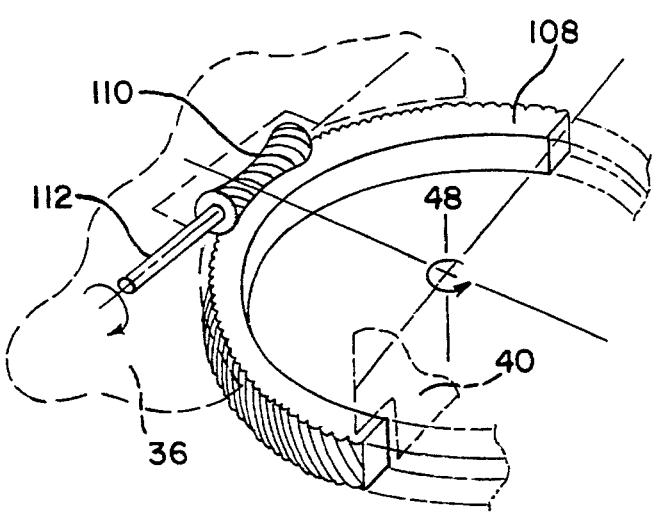
FIG. 10
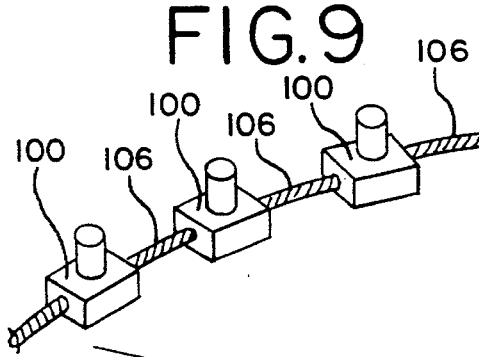
FIG. 9
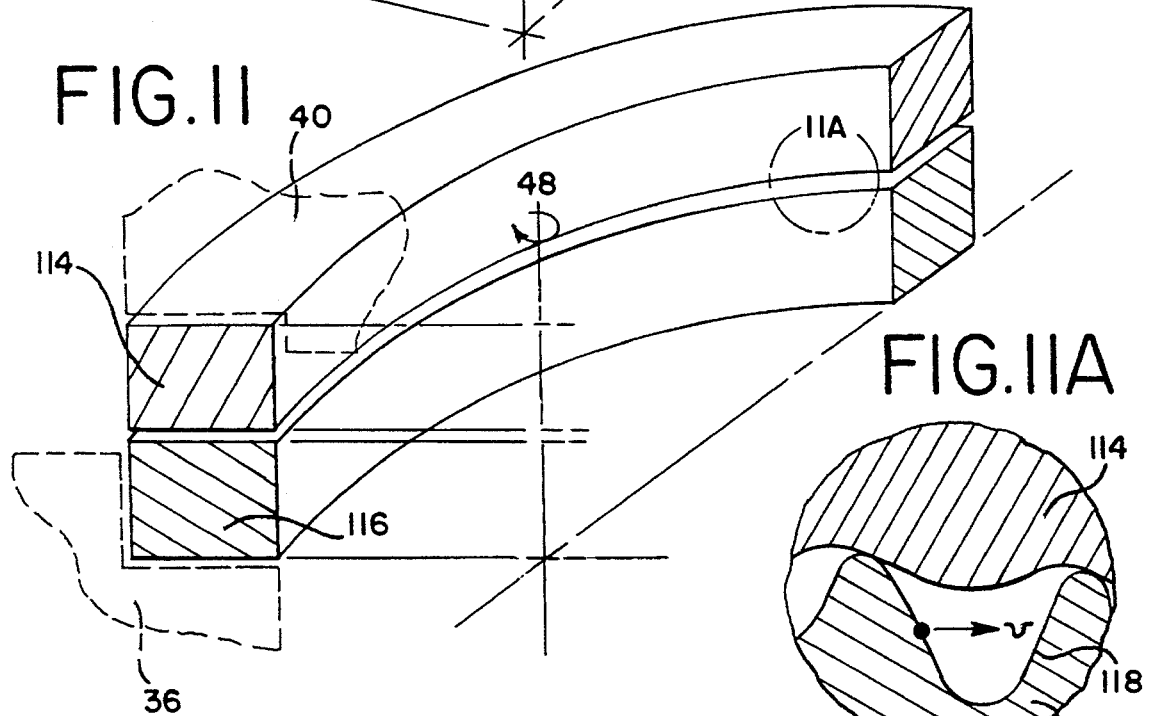
FIG. 11
FIG. 11A

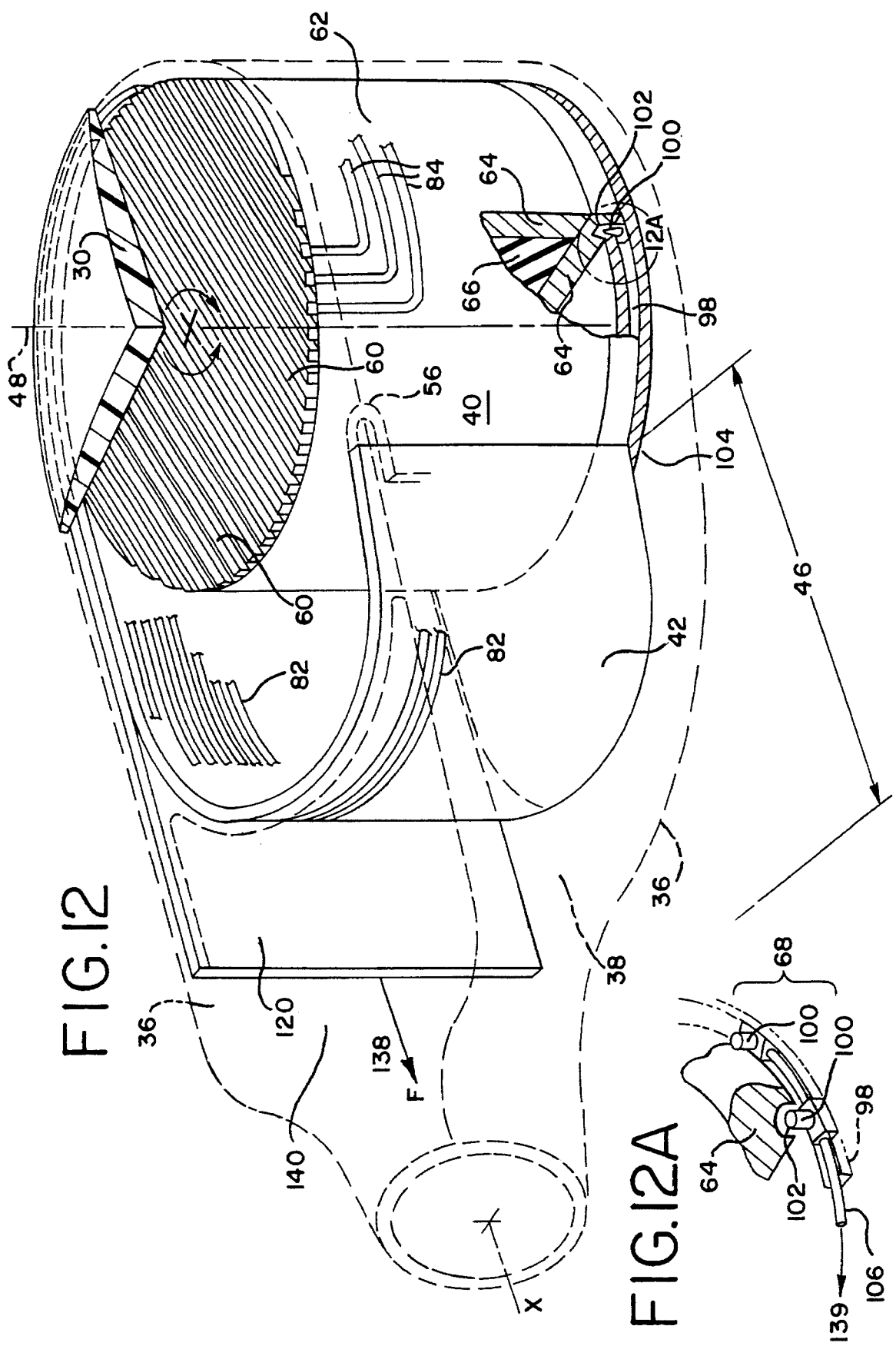

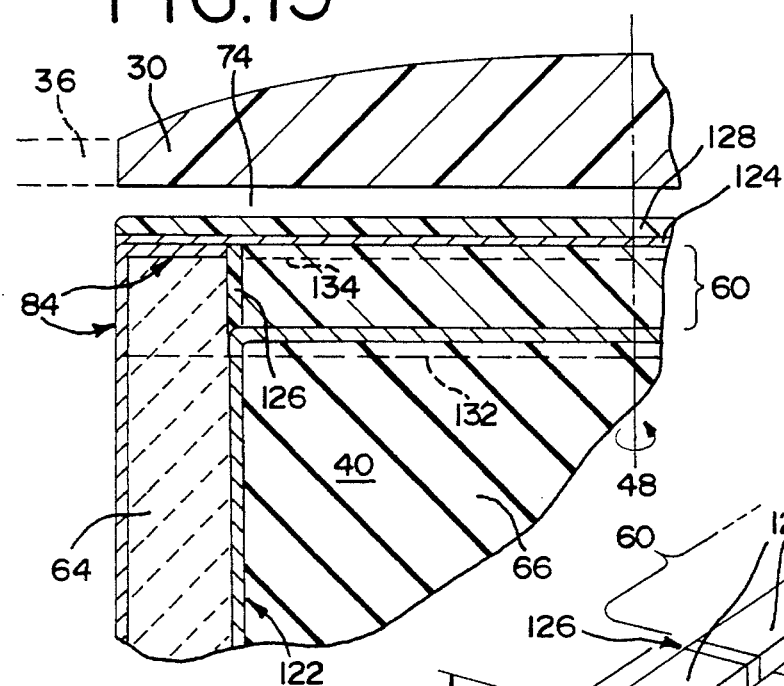
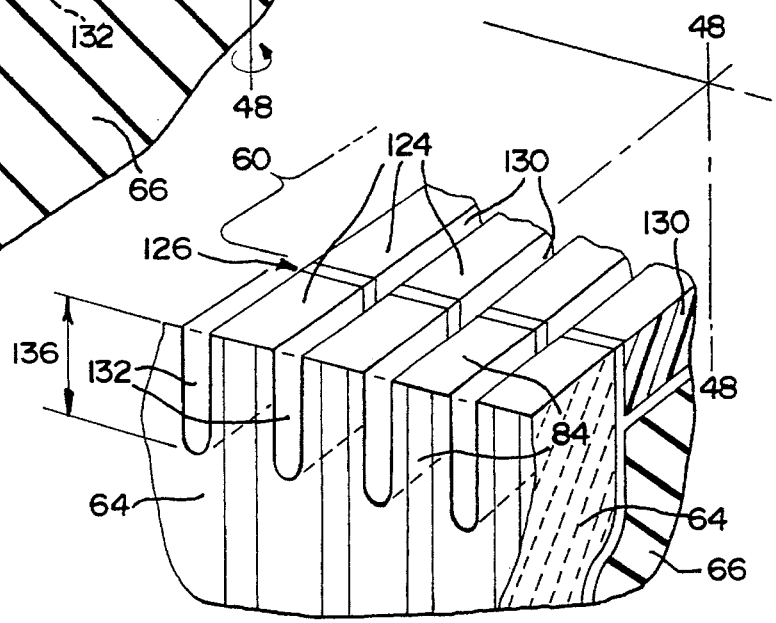
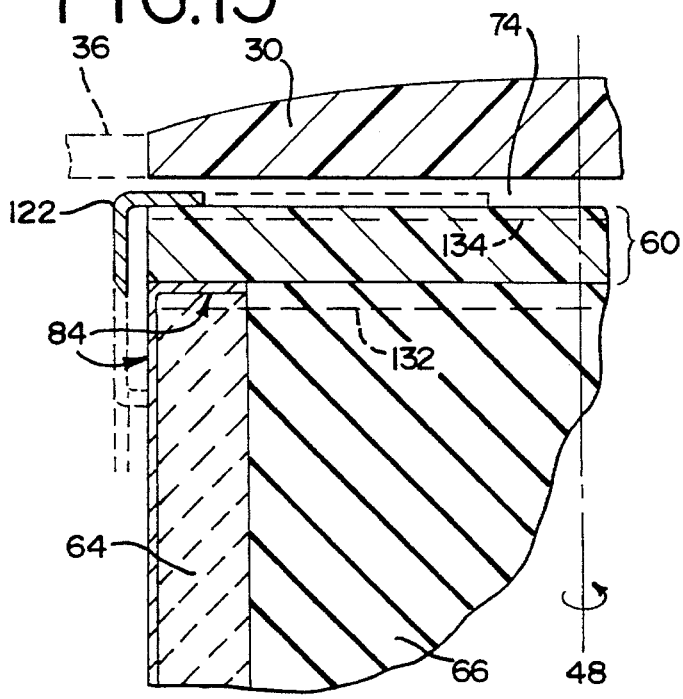

COMPACT ROTATIONALLY STEERABLE ULTRASOUND TRANSDUCER

BACKGROUND OF THE INVENTION

The invention relates to ultrasonic imaging systems, and more particularly to systems that utilize a transducer probe to send ultrasonic signals to a remote ultrasonic imaging system.

The users of medical ultrasound transducer probes, hereinafter referred to as sonographers, can access bodily regions to be imaged via their free hand physical manipulation, rotation, sliding and tilting of the transducer probe. One area in particular where this manipulation is more challenging is transesophageal cardiac imaging. During transesophageal cardiac imaging, the sonographer orients a scanhead at the tip of the transducer probe in the esophagus or stomach of a patient in order to obtain different fields of view of the heart. To obtain the desired views of the heart, the sonographer may have to slide, twist or curl the transducer probe in order to properly position the scanhead, which contains the imaging transducer(s).

For this application, it has been found desirable to rotate the transducer contained in the scanhead independently from the scanhead itself. In combination with the ability to slide, twist or curl the scanhead, the ability to independently rotate the transducer(s) while the scanhead is stationary gives the sonographer the ability to obtain an ultrasonic image of any image plane orthogonal to and intersecting the face of the transducer(s) at each location to which the scanhead can be moved. By giving the sonographer the ability to remotely rotationally orient the acoustic device in the scanhead to obtain different image slices of the heart or its valves, for example, patient comfort is increased. Further, the time required for an ultrasonic examination may be reduced.

Devices are known that incorporate a remotely rotationally adjustable transducer. For example, U.S. Pat. No. 4,543,960 to Harui et. al. discloses a transesophageal echo cardiography scanhead. The elements of the transducer are mounted upon a rotatable base, which is connected by a shaft to a pulley below the transducer. A control cable is directed into the scanhead and is attached to the pulley. The elements of the transducer are electrically connected to a wire bundle by flexible PCB interconnects. The control cable is guided, through a pair of guide tubes, out of the scanhead so that the operator can control the angular relationship of the transducer with respect to the housing.

A disadvantage of the Harui device is that the pulley, shaft and flexible PCB interconnects require a considerable volume within the scanhead. It is desirable to maintain a minimum profile scanhead so that the scanhead may be easily inserted into the body and manipulated therein without causing excessive patient discomfort.

A further disadvantage of the Harui device is that, during rotation of the transducer, bending and axial stresses act upon the flexible PCB interconnects. In addition, the striking of the inner wall of the scanhead by the flexible PCB interconnects during rotation may cause the interconnects to buckle, jam and/or abrade. Because these devices generally cannot be repaired on site if broken and can cause major disruptions for their users and subjects if they fail while inserted in a patient, it is desirable to maximize the reliability of such rotatable probe devices. Additionally, with the device described, the flexible PCB interconnects may not act efficiently as thermal conductors. It is desirable to conduct heat away from the transducer(s) during its operation to avoid a "hot spot" on the scanhead in the lens area above the transducer, which could produce patient discomfort.

Another device incorporating a remotely rotationally adjustable transducer is disclosed in U.S. Pat. No. 5,176,142 to Mason. Mason describes using a rotating cable to drive a gear train within a scanhead of a probe. The gear train rotates a shaft-mounted transducer support structure. The transducer array is linked to conductors connected to the remote imaging electronics by a flex cable assembly. A first portion of the flex cable assembly is embedded in an acoustic damping material, which fills the volume within the support structure. The flex cable assembly protrudes out of the damping material, through an opening in the support structure, and extends around the support structure in the form of a loop. The loop portion of the flex cable assembly becomes straight and extends into a rear volume within the scanhead. In the rear volume, the flex cable assembly is formed into a spiral, which is wrapped around and attached to a stationary post.

A disadvantage of the Mason device is that the flex cable assembly is subjected to bending and axial stresses as the transducer array is rotated by the gear train, and the flex cable assembly may buckle, jam and/or abrade as it is ejected into or pulled from the rear volume. Additionally, the flex cable assembly and the shaft present acoustic discontinuities within the acoustic damping material. It is desirable to minimize acoustic discontinuities in the damping material and to minimize the worst bending excursion, axial buckling potential and abrasion experienced by any portion of the flex cable assembly. Further, the Mason device contains a complex gear train that occupies substantial space within the scanhead and may produce particulate debris that may interfere with the operation of the device.

Accordingly, it would be desirable to have an improved remotely rotationally-steerable medical ultrasound transducer device.

SUMMARY OF THE INVENTION

According to a first aspect of the present invention, an ultrasonic probe for use with a remote ultrasonic imaging system is provided comprising a multielement transducer having an upper surface and a lower surface, an ultrasonically attenuative backing material adjoining the lower surface of the multielement transducer, a container having a wall and a bottom, the attenuative backing material being disposed within the container, a track connected to the container, a flexible assembly attached to the container, and a carrier band attached to the container. The carrier band is operable to rotate the container about an axis defined by the track.

According to a second aspect of the present invention, a compact rotationally steerable ultrasound transducer for use with a remote ultrasonic imaging system and a gastroscope is provided comprising a multielement transducer having an upper surface and a lower surface, an ultrasonically attenuative backing material adjoining the lower surface of the multielement transducer, a container having a cylindrical wall and a bottom, the attenuative backing material being disposed within the container, a flexible assembly having at least two layers wherein one of the layers is a carrier band, each of the layers being connected to the cylindrical wall of the container, and a circular track mounted to the container. The circular track is operable to rotate the multielement transducer.

According to a third aspect of the present invention, a method of forming a near real-time ultrasonic image of at least a portion of a surface that intersects in at most one point an axis of rotation of a remotely rotatable ultrasonic multi-element transducer is provided, comprising the steps of slewing the ultrasonic multielement transducer about the axis of rotation to a plurality of angular positions, scanning a selected scan line within the surface at each angular position, and displaying the selected scan line scanned at each angular position, the displayed scan lines forming the image.

BRIEF DESCRIPTION OF THE DRAWINGS

FIG. 1 is a plan view of a first preferred embodiment of a compact rotationally steerable medical ultrasound transducer probe.

FIG. 2 is a top sectional view of the first preferred embodiment of a compact rotationally steerable medical ultrasound transducer scanhead.

FIG. 3 is a sectional view of the embodiment of FIG. 2.

FIG. 8 is a fifth preferred embodiment of the circular track shown in FIG. 4.

FIG. 9 is a perspective view of a portion of the circular track shown in FIG. 8.

FIG. 10 is a sixth preferred embodiment of the circular track shown in FIGS. 8 and 9.

FIG. 11 is a seventh preferred embodiment of the circular track shown in FIGS. 8 and 9.

FIG. 12 is a cutaway perspective view of a presently preferred embodiment of a compact rotationally steerable medical ultrasonic transducer scanhead.

FIG. 13 is a sectional view of the acoustic device shown in the scanhead of FIG. 12.

FIG. 14 is a perspective view of the acoustic device shown in FIG. 13.

FIG. 15 is an alternative embodiment for the acoustic device shown in FIG. 13.

DETAILED DESCRIPTION OF PRESENTLY PREFERRED EMBODIMENTS

Figure 7:
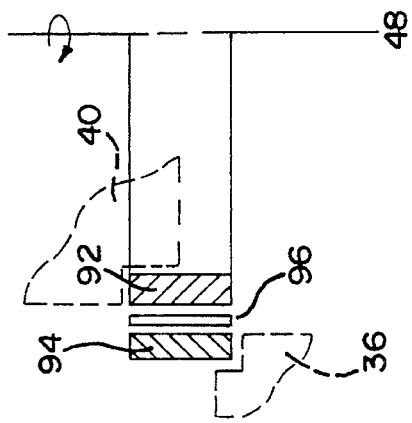
FIG. 7 is a fourth preferred embodiment of the circular track shown in FIG. 4.

FIG. 1 shows a transesophageal echocardiography probe 20 in accordance with the invention. The probe 20 has a control housing 22 upon which one or more control knobs 24 are mounted. A gastroscope 26 extends from the control housing 22. An ultrasonic scanhead 28 having a window 30 is located at a distal end of the gastroscope 26. The control housing 22 is connected to a remote ultrasound system 32 (not shown) by a cable 34.

FIG. 2 is an enlarged section of the ultrasonic scanhead 28 shown in FIG. 1. The scanhead 28 has a housing 36 with a cavity 38 formed therein. The cavity 38 contains an acoustic device 40 and a flexible assembly 42. A carrier band 120 is laminated to or cofabricated with the flexible assembly 42. At one end, the flexible assembly 42 and the carrier band 120 are attached to the circumference of the acoustic device 40 at a location 44. Slack in the flexible assembly 42 is stored in a region 46 of the scanhead cavity 38. The other end of the flexible assembly 42 is electrically connected to a wire bundle (not shown) extending from the gastroscope 26.

The acoustic device 40 is capable of being rotated about an axis 48. As the acoustic device 40 rotates in the direction of arrow 50, the flexible assembly 42 and the carrier band 120 are drawn from the region 46 and co-wrapped around the outer diameter of the acoustic device 40. Phantom outline 52 illustrates the position of the flexible assembly 42 and the carrier band 120 in region 46 after the acoustic device 40 is rotated approximately 180 degrees. The location 44 at which the flexible assembly 42 is attached to the acoustic device 40 is shown in phantom after this rotation at location 54.

A portion of the flexible assembly 42 and colaminated carrier band 120 remains stationary during rotation of the acoustic device 40. A permanent 180 degree bend 56 is formed in the flexible assembly 42 and the carrier band 120. Preferably, the bend 56 is rigidly encapsulated, for example in an epoxy, to insure that it does not flex during operation of the device 40. Alternatively, the bend 56 may slightly deform in an elastic manner during operation. A stationary length 58 of the flexible assembly 42 extends from the bend 56 toward the gastroscope 26 (not shown). The permanent 180 degree bend 56 and the stationary length 58 are preferably anchored to the scanhead housing 36. The portion of the flexible assembly 42 extending from the start of the 180 degree bend 56 toward the gastroscope 26, including the stationary length 58, is hereinafter referred to as the stationary portion of the flexible assembly 42.

The remainder of the flexible assembly 42 may be referred to as the movable portion of the flexible assembly 42. When arranged as shown in FIG. 2, the carrier band 120 moves in unison with the movable portion of the flexible assembly 42. On the movable portion of the flexible assembly 42, the carrier band 120 is shown laminated to the side of the flexible assembly 42 that is nearest the walls of the scanhead housing 36.

As shown in FIG. 2, the flexible assembly 42 may be fabricated from two layers of flexible circuitry 41, 43.

Typically, one of the layers of the flexible circuitry 41, 43 has a plurality of flex interconnect traces 82, shown in FIG. 3, formed thereon or therein, and the other layer is a dielectric insulating layer such as 5 to 35 micron thick polyimide, Parylene™ or Kapton™ film. Other adhesive and cover layers (not shown) may also be utilized. Ultraminiature flat cables suitable for this application are available from Tayco Engineering Incorporated of Cypress, Calif.

The flex interconnect traces 82 may be fabricated using conventional thin-film, thick-film or additive/subtractive plating process techniques while the flexible assembly 42 and carrier band 120 are in a flat state. Typically, the interconnect traces 82 are thin, metallic, fatigue-resistant and lithographically formed interconnects made from gold, copper or alloys thereof. The optimal thickness of the interconnect traces 82 is approximately 5 to 35 microns.

The traces 82 preferably have a net compressive stress as formed in the flat state. The net compressive stress insures that for all points along the length of the flex interconnect traces 82 contained in the movable portion of the flexible assembly 42, the flex interconnect traces 82 remain in a compressive state regardless of the position of the movable portion of the flexible assembly 42. The carrier band 120, if laminated to the face of the flexible assembly 42 that is convex on the movable portion of the flexible assembly 42, will also tend to insure the preferred compressive stress states in the flex interconnect traces 82.

FIG. 3 is a side view of the ultrasonic scanhead 28 shown in FIG. 2. The acoustic device 40 has a multielement transducer 60 mounted on a base 62. The base 62 comprises a container 64 that is filled with an ultrasonically attenuative backing material 66. The container 64 of the acoustic device 40 is mounted on a ring-shaped circular track 68. The circular track 68 is supported by the scanhead housing 36.

A generally flat (shown) or slightly domed (not shown) window 30 is fixed in the scanhead housing 36 above the acoustic device 40. Ultrasound waves may pass in either direction through the window 30. The interface 70 between the window 30 and the housing 36 is sealed to prevent the ingress of damaging disinfectants and sterilizing agents as well as the potential incubation of pathogens.

A cylindrical acoustic lens 72 is attached to the multielement transducer 60. The acoustic lens 72, which may be fabricated of a rubbery material such as RTV silicone, provides elevational focusing to the ultrasound beam. A plurality of electronic time delays associated with the remote ultrasound system 32 (not shown) provide azimuthal beam steering. In the embodiment shown in FIG. 3, the acoustic lens is fixed to and rotates with the multielement transducer 60. Alternatively, the lens 72 may be incorporated into the window 30 that is fixed in the scanhead housing 36, wherein the lens would then be generally hemispherical or domed in shape. As a second alternative, the multielement transducer 60 may be a concave elevationally curved array of piezo-elements, such that the multielement transducer is focussed in the elevation plane without an acoustic lens. The concave curved array, like the multielement transducer 60 with the lens 72, may be azimuthally focussed using electronic time delays.

A material 74 fills the volume between the rotatable acoustic device 40 and lens 72, and the fixed window 30. The material 74 conforms to the lens 72 and the window 30. Preferably, the material 74 comprises an acoustic liquid 76 (not shown) and a secondary filler 78 (not shown), wherein the secondary filler 78 is saturable with the acoustic liquid 76, has significant elastomeric properties, and does not significantly degrade the acoustic properties of the acoustic liquid 76. An example of an acceptable secondary filler 78 is a synthetic hydrophilic polyvinyl alcohol (PVA) permeable flexible membrane, as sold by Kanebo PVA Materials of Elmhurst, Ill. The deformable secondary filler 78 inhibits undesirable liquid currents, which may distort the ultrasound beam.

The secondary filler 78 may be rigidly held along its circumference, by a clamping ring 80, to the rotating acoustic device 40. As an alternative to the secondary filler 78 and acoustic liquid 76, the material 74 may be an appropriate liquid, gel or paste of sufficient viscosity to avoid thermally or rotationally induced currents that may disrupt image quality.

In FIG. 3, a cutaway view of the flexible assembly 42 is shown so that both the stationary portion 56, 58 and the movable portion may be seen. Again, phantom outline 52 illustrates the position of the flexible assembly 42 and the carrier band 120 in region 46 after the acoustic device 40 is rotated approximately 180 degrees about the axis 48. The flexible assembly 42 carries and routes the flex interconnect traces 82 between the rotating acoustic device 40 and the wire bundle (not shown) extending from the gastroscope 26.

At the distal end of the flexible assembly 42, the flex interconnect traces 82 are connected to mating electrically conductive traces 84 on or within the container 64 of the acoustic device 40. Preferably the container 64 is fabricated from a thermally conductive ceramic, such as aluminum nitride, silicon carbide or beryllium oxide, so that the traces 84 may be formed upon or within the container 64 using conventional thick-film or thin-film technology. At the proximal end of the flexible assembly 42, the flex interconnect traces 82 are connected to electrical conductors (not shown) that are routed through the gastroscope 26 to the remote ultrasound system 32.

Because of the mechanical protection and stability provided by the carrier band 120 to the flexible assembly 42, and provided by the container 64, a high density of interconnection between the flex interconnect traces 82 and the electrically conductive traces 84 on the container 64 can be reliably achieved. Consequently, a flexible assembly 42 that is shorter along the axis 48, or a greater number of electrically independent elements 130, shown in FIG. 14, may be utilized. High density tape automated bonding ("TAB") or tight-pitch soldering/welding methods are preferably utilized to electrically connect the flex interconnect traces 82 to the conductive traces 84 on the container 64.

Preferably, the joints between the flex interconnect traces 82 and the traces 84 are strain relieved by bonding the carrier band 120 to the container 64. By having the carrier band 120 wrap around the container 64 beyond the trace 82/trace 84 joints, a region is provided to rigidly bond the carrier band 120 to the circumference of the container 64 as well as to provide a thermally conductive joint for the heat to pass from the container 64 into the carrier band 120.

The carrier band 120 is preferably constructed of a thin elastically bendable material, such as a thin silver alloy or copper alloy band having a thickness of approximately 0.0007 to 0.0100 inches. As an alternative, the carrier band 120 may be fabricated from thin, flexible ceramic or glass. The material should have a high yield strength and excellent fatigue resistance such that all operational deformations are elastic in nature, no mechanical fatigue takes place, and the carrier band 120 is very resistant to localized bending on a small radius, as may otherwise occur in an undesired local buckling event.

If the carrier band 120 is to function as a heat sink, it is preferably fabricated from beryllium copper or silver copper, which are thermally conductive. Alternative thermally conductive materials include silver or copper plated stainless steel or titanium. As another alternative, the thermal conductivity of the carrier band 120 may be greatly increased by coating the carrier band 120 with a thin film vapor-deposited or plasma-deposited diamond layer. The carrier band 120 will radiate heat into the gas or liquid filled scanhead housing 36 or transfer heat directly to the scanhead housing 36 in the region where the carrier band 120 is attached to the scanhead housing 36. By providing an increased heat sinking path, the carrier band 120 allows the acoustic device 40 to be operated at increased acoustic power levels without exceeding the probe's thermal limit. Accordingly, image quality and imaging penetration are improved.

The carrier band 120 may be utilized for electrical functions in addition to its mechanical and/or thermal functions. For example, the carrier band 120 may function as a common electrical ground return or as a common electrical hot lead for the multielement transducer 60. Further, the carrier band 120 may function as an electrical ground reference plane to control the impedance of the flex interconnect traces 82.

FIGS. 4 through 11 show some of the possible configurations for the circular track 68 shown in FIG. 3. One function of the circular track 68 is to provide rotational guidance for the acoustic device 40 and the flexible assembly 42. More particularly, the circular track 68 ensures that the acoustic device 40 rotates only about the axis 48 defined by the circular track 68 so that the rotational driving mechanism employed does not have to overcome binding and jamming of the rotating acoustic device 40. Further, the circular track 68 provides rotational guidance without using an axial shaft, which would disrupt the acoustic integrity of the attenuative backing material 66. A simple circular track 68 that provides rotational guidance may be formed by placing a raised circular lip about the axis 48 on the floor of the scanhead housing 36. A mating circular groove or ridge would be provided on the bottom of the container 64. Additional functions that the circular track 68 may perform include driving of the rotational motion, clamping and fastening the acoustic device 40 to prevent undesired motions along the axis 48, and braking or clutch functions.

Figure 4:
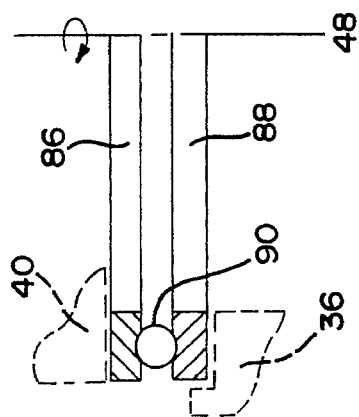
FIG. 4 is a radial section of a circular track in the scanhead of FIG. 3.

FIG. 4 shows a radial section of one embodiment of the circular track 68. In this embodiment, the circular track 68 comprises a ringshaped roller or ball bearing. The acoustic device 40 is attached to a rotating ring 86, which rotates about the axis 48. A stationary ring 88 is fixed to the scanhead housing 36. Ball bearings 90 are located between the stationary ring 88 and the rotating ring 86. Cylindrical or tapered cylindrical rollers may be used in place of ball bearings 90. Retainers or other devices customarily used to hold bearing components together are not shown in the Figures.

Figure 5:
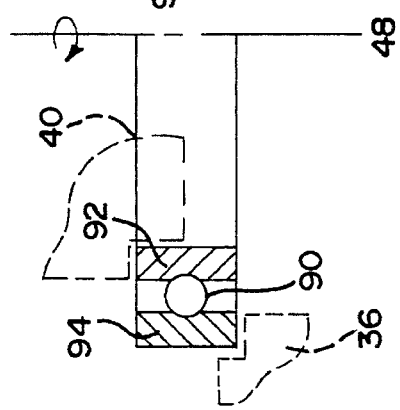
FIG. 5 is a second preferred embodiment of the circular track shown in FIG. 4.

FIG. 5 shows a radial section of an embodiment of the circular track 68 that is similar to the ring-shaped roller or ball bearing shown in FIG. 4. The acoustic device 40 is attached to an inner rotating ring 92, which rotates about the axis 48. An outer stationary ring 94 is centered about and coaxial with the axis 48 and fixed to the scanhead housing 36. Ball bearings 90 are located between the outer stationary ring 94 and the inner rotating ring 92.

Figure 6:
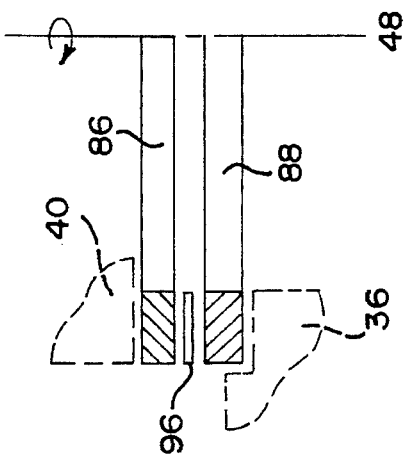
FIG. 6 is a third preferred embodiment of the circular track shown in FIG. 4.

FIGS. 6 and 7 show embodiments of the circular track 68 that are similar to the embodiments shown in FIGS. 4 and 5 respectively. The ball bearings 90, however, are replaced with a lubricating layer 96, such as a polytetrafluoroethylene film, that allows relative nonbinding sliding motion of the rings 86 and 88 or 92 and 94. The lubricating layer 96 may be a free standing film or may be a coating on one or both of the mating surfaces of the rings 86 and 88 or 92 and 94. The embodiments of the circular track 68 shown in FIGS. 6 and 7 guide the acoustic device 40 in rotational motion about the axis 48.

The embodiments of FIGS. 4 through 7 provide rotational guidance to the acoustic device 40, as well as fixing the three dimensional position of the acoustic device 40, in very compact dimensions. In the embodiments shown, the rotating ring 86 or inner rotating ring 92 may be integrated into the container 64 of the acoustic device 40. Similarly, the stationary ring 88 or outer stationary ring 94 may be integrated into the scanhead housing 36. Additionally, an extremely low profile air-supported bearing could be formed by replacing the ball bearings 90 in FIGS. 4 and 5 or the lubricating layer 96 in FIGS. 6 and 7 with a thin film of externally sourced compressed air, which is exhausted through the gastroscope 26. A plurality of air channels may be formed in the mating rings of the air-supported bearing.

FIGS. 8 and 9 show an embodiment of the circular track 68 that is capable of driving the rotation of the acoustic device 40 in addition to providing rotational guidance. In FIG. 8, a radial section about the axis 48 of the acoustic device 40 and the scanhead housing 36 is shown. A preferably reentrant groove 98 is formed in the surface 104 of the scanhead housing 36. The reentrant groove 98 is circular in shape and is centered about the axis 48. At least one pin or peg 100 is slidably mounted in the groove 98. Each pin or peg 100 interlocks with a mating hole 102 or similar abutting edge feature, such as a ledge, formed in the bottom of the rotatable acoustic device 40.

FIG. 9 shows a sliding chain or wire 106 to which several of the pins or pegs 100 are firmly attached. This assembly may be placed in the circular reentrant groove 98, shown in FIG. 8, in the surface 104 of the scanhead housing 36. The chain or wire 106 may be a woven or single-strand polymeric, glass, ceramic or metal fiber, cord, band, wire or multi-link miniature chain. As an example, a KEVLAR™ fiber or band could be utilized.

FIG. 10 shows an alternative embodiment of the circular track 68 that is capable of driving the rotation of the acoustic device 40 in addition to providing rotational guidance. The acoustic device 40 is attached to a toothed ring 108, the toothed ring 108 being centered about the axis 48. The toothed ring 108 engages a toothed worm gear 110, which is driven by a torsional control cable 112. In addition, the toothed ring 108 may be provided with a groove or bearing surface (not shown) to rotate in or around so that the toothed ring 108 may be kept centered about the axis 48. Alternatives to the worm gear shown in FIG. 10 include a bevel gear, hypoid gear or a spur gear.

In FIG. 11, another embodiment of the circular track 68 is shown. This embodiment is capable of driving the rotation of the acoustic device 40 and of providing rotational guidance. In addition, this embodiment is capable of providing rotational position sensing.

FIG. 11 shows the acoustic device 40 attached to a rotor ring 114. A stator ring 116 is positioned below the rotor ring 114 and is fixed to the scanhead housing 36. The rotor ring 114 and the stator ring 116 are centered about the axis 48. The rotor ring 114 and the stator ring 116 together comprise a piezomotor capable of piezoelectrically driving and guiding the acoustic device 40. In the expanded view of the interface between the rotor ring 114 and the stator ring 116, a travelling sine wave 118 is shown. As will be recognized by those skilled in the art, the torsional driving force is derived from piezoelectrically created traveling sine waves in the interface between the rotor ring 114 and the stator ring 116.

Piezomotors, such as that formed by rings 114 and 116, can be very small, can achieve continuous rotation as well as stepping rotation, have intrinsically high torque at all speeds, and act as brakes when not energized. Further, piezomotors do not require the use of a central motor shaft. The ring shaped piezomotor 114/116 as shown is preferred, although the piezomotor may alternatively be disc shaped. Where the piezomotor is used to drive the rotation of the acoustic device, the use of rotational control cables passing from the control housing 22, shown in FIG. 1, into the scanhead housing 36 is eliminated. Finally, a rotational position sensor may be incorporated into the piezomotor as described in S. Segawa et. al., *Ultrasonic Piezomotor Equipped with a Piezoelectric Rotary Encoder*, IEEE Ultrasorties Symposium 1205–09 (1990).

FIG. 12 shows a sectioned perspective view of a rotatable acoustic device 40 according to the present invention. The acoustic device 40, as previously described in relation to FIG. 2, has a multielement transducer 60 mounted on a base 62. The base 62 is a container 64 that is filled with an attenuative backing material 66. Electrical traces 84 are formed on the external surface of the container 64. A generally flat window 30, or a hemispherical or domed combination lens/window 30, is fixed in the scanhead housing 36 above the acoustic device 40. The hemispherical lens/window 30 provides elevational focusing for any rotational position of the acoustic device 40.

The acoustic device 40 is attached to the embodiment of the circular track 68 shown in FIGS. 8 and 9. As shown in FIG. 12, the pegs 100, which are connected to the sliding band 106, project from the reentrant groove 98 formed in the surface 104 of the scanhead housing 36. Each peg 100 interlocks with a mating hole 102 in the container 64 of the acoustic device 40. The acoustic device 40 may rest directly upon the sliding band 106 and/or the pegs 100. Alternatively, the acoustic device 40 may rest on the surface 104 and be dragged in rotation by the pegs 100.

The container 64 may be formed of two pieces. A first circular piece forming the bottom and a second cylindrical piece forming the sides of the container 64. This allows the circular bottom piece to be fabricated with materials, coatings and features that optimize the mechanical mating and tribological considerations of the sliding band 106/peg 100/ surface 104 to container 64 interface.

FIG. 12 also shows the flexible assembly 42, having flex interconnect traces 82, described above with reference to FIGS. 2 and 3. In the embodiment of FIG. 12, the flex interconnect traces 82 are disposed on one or both (shown) faces of the flexible assembly 42. Further, the carrier band 120 is co-wrapped with the flexible assembly 42 around the acoustic device 40, but, in this embodiment, is not laminated or otherwise attached to the flexible assembly 42. The carrier band 120 and the flexible assembly 42 are attached to the circumference of the acoustic device 40 such that the flexible assembly 42 is positioned between the carrier band 120 and the container 64. In this manner, the carrier band 120 protects the flexible assembly 42 from abrasive damage.

Figure 16:
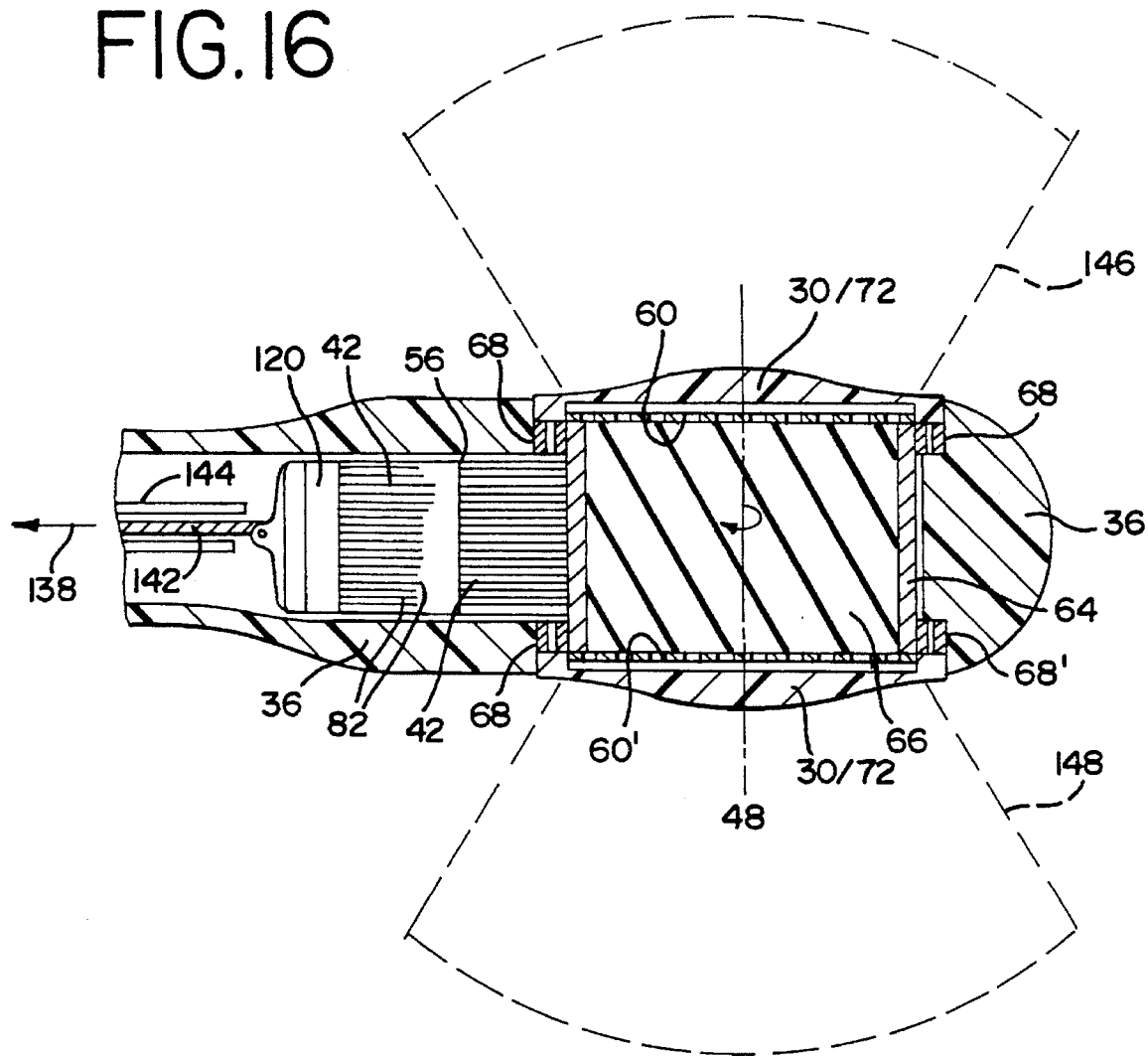
FIG. 16 is a sectional view of a presently preferred embodiment of the compact rotationally steerable medical ultrasound transducer having two comfortable multielement transducers.
Figure 17:
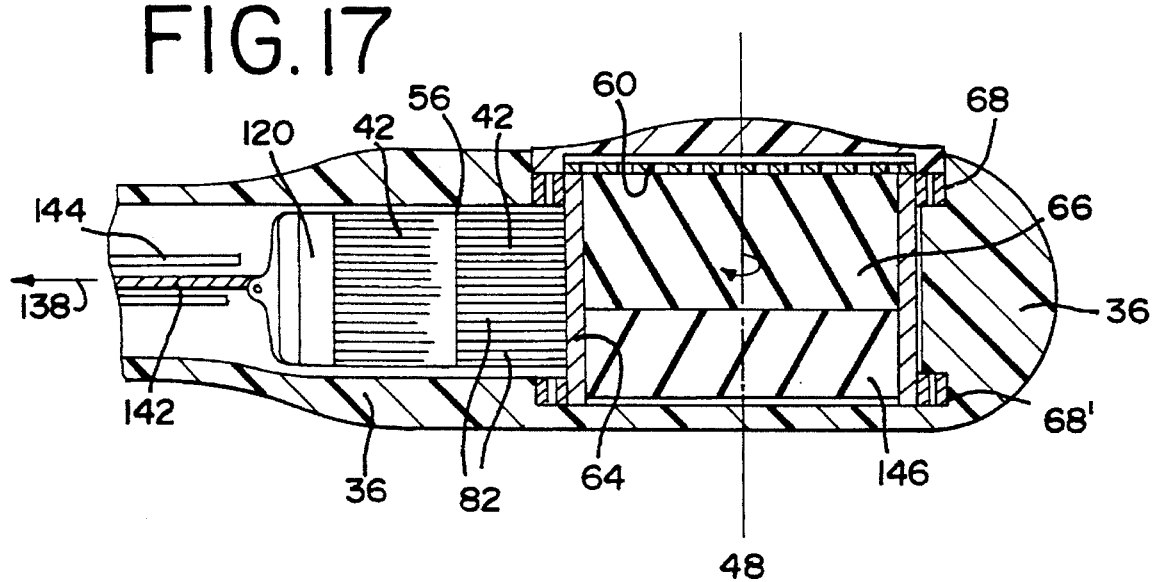
FIG. 17 is a sectional view of a presently preferred embodiment having a magnetic position sensor co-rotatable with the multielement transducer.

The flexible assembly 42 is otherwise disposed within the scanhead cavity 38 as shown in FIGS. 2 and 3. In particular, the flexible assembly 42 has a stationary portion, including the 180 degree bend 56, where the flexible assembly 42 reverses direction to provide the flex interconnect traces to the back of the scanhead housing 36 and the gastroscope 26, shown in FIG. 1. The carrier band 120 may also contain termination hardware (not shown), which allows mating of the carrier band 120 to a control cable or wire 142, as shown in FIGS. 16 and 17, extending from the gastroscope 26 into the scanhead housing 36. The termination hardware may prevent the carrier band 120 from distorting in an undesirable manner, in the region where the control cable or wire 142 is connected to the carrier band 120, when the control cable or wire 142 pulls upon the carrier band 120. Although both the carrier band 120 and the circular track 68 shown in FIG. 12 are capable of driving the rotation of the acoustic device 40, only one driving mechanism is needed.

FIGS. 13 and 14 show how the acoustic device 40 of the preferred embodiment is constructed. In FIG. 13, the acoustic device 40 is positioned below the window 30 that is fixed in the scanhead housing 36. The material 74, described above in reference to FIG. 3, separates the rotatable acoustic device 40 from the window 30. In the embodiment shown in FIGS. 13 and 14, the lens 72, shown in FIG. 3, is incorporated into the window 30. The axis 48 about which the acoustic device 40 rotates is shown for reference only.

FIG. 13 shows the attenuative backing material 66 located within the cylindrical container 64. At least one electrically conductive ground electrode 122 passes through the interface between the attenuative backing material 66 and the inner wall of the container 64 and across the upper surface of the attenuative backing material 66. The multielement transducer 60 is positioned within the cylindrical container 64 on top of the ground electrode 122 that passes across the upper surface of the attenuative backing material 66, such that the array 60 is generally flush with the top edge of the cylindrical container 64.

FIGS. 13 and 14 show the electrically conductive traces 84 that have been formed on the outer surface of the container 64 as discussed above with respect to FIG. 3 and as shown in FIGS. 3 and 12. Preferably, the conductive traces 84 pass over the top edge of the cylindrical container 64 as shown in FIG. 13.

A metal film layer 124 interconnects the electrically conductive traces 84 and the multielement transducer 60. An epoxy or other filler material may provide a smooth physical bridge 126 between the inner wall of the container 64 and the multielement transducer 60. The multielement transducer 60 may have a metalization layer (not shown) on its upper surface to facilitate electrical connection between the multielement transducer 60 and the metal film layer 124. An insulating layer 128 overlies metal film layer 124. The layer 128 may be KAPTO™ with the metal film layer 124 formed upon it using known processing techniques. Additionally, the insulating layer 128 may be of a thickness and acoustic impedance such that it serves as an acoustic matching layer. Alternatively, an acoustic matching layer may be provided on top of the insulating layer 128, or the metal film layer 124 may be formed directly upon the multielement transducer 60 in which case the insulating layer 128 serves only as an acoustic matching layer.

In one preferred embodiment, the metal film layer 124 and the insulating layer 128 are cofabricated independently as a flexible circuit having at least one thin polymer material serving as the insulating layer 128 and a patterned metalization layer serving as the metal film layer 124. KAPTON™, UPILEX™ or MYLAR™, with or without an added adhesive film, may be utilized to fabricate the polymer material. The metalization layer may be nickel, gold or gold-plated copper. The adhesive layer, if utilized, may be used between the insulating layer 128 and the metal film layer 124 as is known in the manufacture of flexible circuitry, although the adhesiveless bilayer construction shown in FIG. 13 is preferable acoustically.

Alternatively, the metal film layer 124 may be formed by directly depositing a metalization layer on top of the multielement transducer 60, the top edge of the container 64 and the bridge 126 using an electroplating, electroless plating, vapor-deposition or other thin-film or thick-film deposition process. Deposition masking may be utilized to protect the electrically conductive traces 84 on the outer surface of the container 64 or, alternatively, the metal film comprising the traces 84 may be deposited with the metal film layer 124 without using a deposition mask. After the metal film layer 124 is deposited, it may be patterned as required using known lithographic or laser techniques. If the metal film comprising the electrically conductive traces 84 is deposited with the metal film layer 124, the same patterning techniques may be used to pattern the electrically conductive traces 84 as are used to pattern the metal film layer 124.

FIG. 14 is a perspective view of the acoustic device shown in FIG. 13. The multielement transducer 60 has a number of electrically independent elements 130 separated by dicing kerfs 132 formed by dicing an initially contiguous piezoelectric material. If the metal film layer 124 is formed by directly depositing a metalization layer on the top of the initially contiguous piezoelectric material, the top edge of the container 64, and the filler material 126, then the metal film layer 124 may, as an alternative, be patterned by appropriate dicing after the metalization is deposited. In particular, the surface of the acoustic device 40 may be diced so that each electrically conductive trace 84 on the outer surface of the container 64 is aligned with and electrically connected to only one of the electrically independent elements 130. Although the physical bridge 126 between the inner wall of the container 64 and the multielement transducer 60 is shown in FIG. 14 for clarity, it would not be visible through the metal film layer 124.

The dicing kerfs 132, as shown in FIG. 14, extend through the wall of container 64 and are cut to a depth 136. The depth 136 must be great enough to form the electrically independent elements 130. Accordingly, as shown in outline in FIG. 13, the dicing kerfs 132 extend below the depth of the ground electrode 122. In this manner, the acoustic elements 130, along with their electrodes, the metal film layer 124 and the ground electrode 122, are acoustically and electrically isolated from each other, as is required.

As an alternative to the initially contiguous piezoelectric material, the multielement transducer 60 may be fabricated from a composite construction of piezoelectric elements and a polymeric filler material. Dicing of the composite material is not necessarily required and the acoustic elements 130 may be electrically isolated by appropriate patterning of the metal film layer 124.

FIG. 15 shows an alternative arrangement to the arrangement of the container 64, attenuative backing material 66 and multielement transducer 60 shown in FIGS. 13 and 14. In the embodiment of FIG. 15, the multielement transducer 60 is laminated to the electrically conductive traces 84 on the top edges of the cylindrical container 64. A ground electrode 122 is connected to the top surface of the array 60. Preferably, the multielement transducer 60 has a thin film metalization layer on its top and bottom surfaces so that the ground electrode 122 and the electrically conductive traces 84 may be connected to the thin film metalization at the edge of the array 60.

An advantage of the approach of FIG. 15 is that the depth of the dicing kerf 132 projecting into the container 64 is substantially reduced in comparison to the depth of the dicing kerf 132 projecting into the container 64 as shown in FIGS. 13 and 14. Because of the fragility of the edges of the container 64, it is desirable to minimize the depth of the dicing kerf 132 projecting into the container 64. In addition, when using the construction of FIG. 15, it is not necessary to have an electrode, such as ground electrode 122 shown in FIG. 13, pass along the inner wall of the container 64. A disadvantage of the embodiment shown in FIG. 15 is that undesirable acoustic coupling between the multielement transducer 60 and the container 64 will be greater because of the direct bond between them.

A compromise between the arrangements of FIGS. 13 and 15 may be used in which the outer edge of the multielement transducer 60 is generally coincident with the inner wall of container 64, as shown in FIG. 13, but the bottom surface of the multielement transducer 60 is generally aligned with the top edge of container 64, as shown in FIG. 15. This embodiment of the acoustic device 40 alleviates the acoustic coupling between the multielement transducer 60 and the container 64.

As described with reference to FIGS. 13 through 15, the electrically conductive traces 84 are electrically connected to the electrically independent elements 130 of the multielement transducer 60, either directly or through metal film layer 124. The electrical connection to each electrically independent element 130 of the multielement transducer 60 enables each element 130 to be selectively pulsed or placed in a receive mode.

The operation of the preferred embodiments will now be described in greater detail. Referring to FIG. 1, a transesophageal echocardiography probe 20 in accordance with the present invention is shown. The control housing 22 of the probe 20 contains the mechanical means for bending the tip region of the gastroscope 26 to effect good acoustical contact between the anatomy of interest and the ultrasonic scanhead 28. Typically, the control housing 22 will have one control knob 24 for each plane in which the tip of the gastroscope 26 may be manipulated. Typically, the gastroscope 26 would contain at least one tensioned guide wire or control cable (not shown) for each control knob 24 in order to transmit the bending forces by selective manipulation of the guidewire tensions in the tip region via the control knob(s) 24. Also contained within the probe 20 are the electrical connections between the ultrasonic scanhead 28 and the remote ultrasound system 32 and mechanical connections between the ultrasonic scanhead 28 and the control housing 22.

The electrical connections transmit power from the ultrasound system to the acoustic device 40 and transmit electrical signals produced by the multielement transducer 60 to the ultrasound system. In addition, the electrical connections may transmit temperature indicating and/or positional signals or data. As shown in FIGS. 2, 3 and 12, the flex interconnect traces 82 within or upon the flexible assembly 42 carry the electrical signals within the cavity 38 of the scanhead housing 36. The flex interconnect traces 82 are connected to mating electrically conductive traces 84 formed upon or within the container 64.

For a transesophageal echocardiography device, one desires a multielement transducer that is capable of 180 degrees of unrestricted rotational motion. To achieve this, the flexible assembly 42 should be designed so that in the wound up state virtually all of the movable portion of the flexible assembly 42 is wrapped around the acoustic device 40 and there is minimal to no excess movable portion of the flexible assembly 42 residing in region 46 of the scanhead housing 36. In this manner, the amount of the flexible assembly 42 to be unwound during rotation of the acoustic device 40 through 180 degrees amounts to a length of approximately one-half of the circumference of the acoustic device 40. For clarity, the flexible assembly 42 shown in FIGS. 2 and 3 exaggerates the lineal length necessary for 180 degree rotation and full unwinding.

Mechanical connections between the ultrasonic scanhead 28 and the control housing 22 may be utilized to rotate the acoustic device 40. Referring again to FIGS. 2 through 12, several preferred arrangements of the carrier band 120, the flexible assembly 42 and the circular track 68 are described for driving rotation of the acoustic device 40. In a first preferred arrangement, the circular track 68 drives rotation of the acoustic device 40 and, as shown in FIG. 2, the carrier band 120 is laminated to or formed integrally with the flexible assembly 42, the carrier band 120/flexible assembly 42 being co-wrapped around the acoustic device 40. In a second preferred arrangement, the circular track 68 drives rotation of the acoustic device 40 and, as shown in FIG. 12, the carrier band 120 is co-wrapped with the flexible assembly 42 around the acoustic device 40 but is not laminated to or formed integrally with the flexible assembly 42. Alternative constructions for the circular track 68 that are capable of driving rotation of the acoustic device 40 have been described with reference to FIGS. 8 through 11.

Referring again to FIG. 12, the operation of the first and second preferred arrangements of a remotely rotationally steerable medical transducer, wherein the circular track 68 drives rotation of the acoustic device 40 in addition to providing rotational guidance, will be described. The peg and chain embodiment of the circular track 68 will be described, although the alternative constructions of the circular track 68, shown in FIGS. 10 and 11, could also be used to drive rotation of the acoustic device 40.

The circular track 68 includes a reentrant groove 98 located in the surface 104 of the scanhead housing 36. A sliding band 106 having pegs 100 attached thereto is positioned within the groove 98. As discussed with respect to FIG. 12, each peg 100 interlocks with a mating hole 102 in the bottom of the container 64 of the acoustic device 40. The band 106 may be fabricated from KEVLAR™ polymer, of circular or rectangular cross-section, having the pegs 100 fused to it or molded to it directly.

The inside of the reentrant groove 98 may be lubricated by a disposed lubricant, by surface treatments, or by the use of a self-lubricating material from which the groove 98 is formed, molded or machined. The reentrant groove 98 may be fabricated of machined sapphire, a commonly used high quality bearing material. This provides the sliding band 106 with a slippery and wear-resisting groove 98 in which to slide.

A control wire or cable 142 (not shown) extends into the scanhead housing 36 from the gastroscope 26 and is attached to one end of the sliding band 106. The reentrant groove 98 will diverge from a truly circular shape in the region where the control wire 142 is connected to the band 106. Preferably, the groove 98 is formed such that it directs the band 106 downwards and away from the bottom side of the acoustic device 40 at the region where the band 106 and the reentrant groove 98 diverge from the truly circular shape. Laser or ultrasonic machining of sapphire may be utilized to form the regions of the reentrant groove 98 wherein the sliding band 106 and the groove 98 are directed away from the bottom of the container 64. By forming the groove 98 to direct the band 106 downward, abrasion between the band 106, pegs 100 and the bottom of the container 64 can be avoided.

A driving force applied in a direction 139 to the sliding band 106 is exerted by the control cable or wire 142. As the driving force is applied to the sliding band 106, the band 106 slides within the groove 98 causing the acoustic device 40 to rotate in a clockwise direction about the axis 48. The driving force is preferably generated by a linear piezomotor located in the control housing 22, where the linear piezomotor is attached to the control wire 142. The linear piezomotor is capable of producing very smooth motions and is able to accurately step or index the rotational motion of the acoustic device 40 so that accurately located image planes may be obtained. The linear piezomotor may also be adjusted to account for any stretching or compression of the control wire 142. A suitable commercially available linear piezomotor for this application is the INCHWORM™ linear piezomotor manufactured by Burleigh Instruments, Inc. of Fishers, New York. Alternatively, the force driving rotation may be generated by a linear actuator.

A sliding band 106 without pins or pegs 100 may alternatively be used to rotate the acoustic device 40. In this driving arrangement, the acoustic device 40 rests directly on the portion of the sliding band 106 that moves in true circular motion. An axial bias spring may be utilized to create a mechanical downward preload on the acoustic device 40 pressing it against the sliding band 106 to provide enough friction such that the band 106, or the band 106 and peg 100 system, may drag or carry the acoustic device 40 without slippage.

In the case where a single control wire is connected to one end of the sliding band 106, a torsional spring (not shown) under or around the acoustic device 40 may be used to torsionally preload the acoustic device 40 so that the control cable 142 works against the spring's resistance. Alternatively, two control wires may extend into the scanhead housing 36 through the gastroscope 26, each being attached to an opposite end of the sliding band 106 to drive rotation in either direction. The carrier band 120 ensures that the largest radius of curvature that can be formed by the movable portion of the flexible assembly 42, at each degree of winding or unwinding, will be maintained.

In a third preferred arrangement, the carrier band 120 drives rotation of the acoustic device 40, while the circular track 68 passively guides rotation about the axis 48. The carrier band 120 of the third preferred arrangement is co-wrapped with the flexible assembly 42 around the acoustic device 40, but is not laminated to the flexible assembly 42, as shown in FIG. 12. In this arrangement, the driving force 138, shown in FIG. 12, is supported by the carrier band 120 and not the flexible assembly 42. Alternative constructions for the circular track 68 that are capable of passively guiding the acoustic device 40 in rotation about the axis 48 have been described with reference to FIGS. 4 through 7.

Referring again to FIG. 12, the operation of the third preferred arrangement of a remotely rotationally steerable medical transducer, wherein the carrier band 120 drives rotation of the acoustic device 40, will be described. As shown in FIG. 12, the acoustic device 40 is mounted on the circular track 68. The peg and chain embodiment of the circular track 68, described with reference to FIGS. 8 and 9, is illustrated, although the alternative constructions shown in FIGS. 4 through 7 are preferred for the arrangement wherein the carrier band 120 drives rotation. The carrier band 120 is co-wrapped with the flexible assembly 42 around the acoustic device 40. The carrier band 120 is not, however, laminated or attached to the flexible assembly 42 in the region 46 of the scanhead housing 36. The carrier band 120 is connected to a sliding control cable or wire 142 (not shown), which passes through the gastroscope 26 in a guidetube (not shown) to the control housing 22. A torsional spring (not shown) under or around the acoustic device 40 may be used to torsionally preload the acoustic device 40 so that the control cable 142 works against the spring's resistance. The sonographer may manipulate the control cable 142, using the linear piezomotor or linear actuator in the control housing 22, to exert a driving force in the direction 138 on the carrier band 120, thereby causing the acoustic device to rotate counter-clockwise about the axis 48. Where, as here, the carrier band 120 is used to drive rotation of the acoustic device 40, the circular track 68 acts passively to fix rotation about the axis 48.

As the sliding control cable pulls the carrier band 120, causing the acoustic device 40 to rotate in the counter-clockwise direction in the embodiment shown, the torsional spring (not shown) winds and the movable portion of the flexible assembly 42 and the carrier band 120 unwrap from the acoustic device 40 in a controlled manner. By directing the driving force to rotate the acoustic device 40 through the carrier band 120 and by positioning the carrier band 120 between the flexible assembly 42 and the wall 140 of the scanhead housing 36, the flexible assembly 42 and the flex interconnect traces 82 thereon will be unwrapped from the acoustic device 40 in a manner that protects the flexible assembly 42 and the traces 82 from abrasion, buckling and rubbing against the surfaces of the scanhead housing 36, as well as from any substantial axial loading. As the driving force in the direction 138 on the carrier band 120 is released, the flexible assembly 42 and the carrier band 120 are rewound about the acoustic device 40 by the unwinding torsional spring (not shown).

The driving force in the direction 138 on the carrier band 120 exerted by the control cable or wire 142 (not shown) is preferably generated by a linear piezomotor, as described above, located in the control housing 22. Alternatively, the force driving rotation may be generated by a linear actuator.

Where the circular track 68 acts passively, as described above, any of the embodiments of the circular track 68 illustrated in FIGS. 4–7 may alternatively be used. In addition, it is not necessary that the circular track 68 be located below the acoustic device 40 as shown in FIG. 12. It is envisioned that the circular track 68 could be located above the acoustic device 40 or at any height around the outer circumference of the acoustic device 40. Furthermore, more than one circular track 68 may be used in any of the embodiments described herein.

In another preferred embodiment, a rotationally steerable transducer probe is provided having two opposed multielement transducers 60, 60' as shown in FIG. 16. Two circular tracks 68 and 68' are disposed about the circumference of the container 64. For the apparatus shown in FIG. 16, rotation of the multielement transducers 60 and 60' is effected as described above with respect to the third preferred arrangement using the carrier band 120 connected to the sliding control cable 142. Alternatively, one or both of the circular tracks 68 and 68' may drive the rotation of the two opposed multielement transducers in accordance with either the first or second preferred arrangement described above.

The sliding control cable 142 passes through the gastroscope 26 in a guide tube 144. A linear piezomotor or linear actuator (not shown) contained within the control housing 22 is attached to the sliding control cable 142. A torsional spring (not shown) under or around the acoustic device 40 may be used to torsionally preload the acoustic device 40 so that the control cable 142 works against the spring's resistance.

The acoustic fields of view 146 and 148 are indicated by phantom outlines. Each of the multielement transducers 60 and 60' may be optimized for typically incompatible acoustic functions, such as for two imaging formats or two widely different operational frequencies. The multielement transducers 60 and 60' utilize the same attenuative backing material 66 and container 64. The multielement transducers 60 and 60' would typically be operated individually, although, if the operation of the transducers 60 and 60' is electronically interleaved and simultaneous acoustic contact on both sides of the scanhead 36 can be achieved, the transducers 60 and 60' may be operated simultaneously to perform dual direction imaging.

Another alternative to the preferred embodiments described above is shown in FIG. 17. The multielement transducer 60 is rotated as described above with respect to the third preferred arrangement using the carrier band 120 connected to the control cable 142. Again, although the third preferred arrangement is shown, the first or second preferred arrangements, wherein the multielement transducer is driven by a circular track 68, may alternatively be used.

Two circular tracks 68 and 68' are attached to the outer wall of the container 64. In this embodiment, the attenuative backing material 66 is placed in the container 64 above a magnetic position sensor 146. The magnetic position sensor 146 rotates with the multielement transducer 60 as both are rigidly attached to the rotating container 64. A remote transmitter (not shown) generates magnetic fields that are detected by the magnetic position sensor 146 attached to the container 64°. The magnetic position sensor 146 may be electrically connected in a manner similar to that of the electrically independent elements 130 of the multielement transducer 60, wherein flex interconnect traces 82 resident on the flexible assembly 42 and electrically conductive traces 84 on the outer surface of the container 64 are utilized. The magnetic position sensor 146 is capable of indicating the rotational and angular position of the transducer 60, as well as the position of the scanhead 36 within the patient.

The remote acoustic imaging system 32 receives real-time rotational and spatial position information so that the spatial positions of image planes can be recorded, or the acquisition of the image planes may be triggered at desired rotational orientations, angles or positions. The magnetic position sensor 146 may also be used to trigger the acquisition of multiple parallel image planes obtained as the scanhead 28 is dragged axially along the esophagus wall with its imaging plane generally perpendicular to the direction of dragging. During use in this mode, the device is not rotated as it is dragged. In these manners, three-dimensional image sets can be directly obtained using a two-dimensional multielement transducer 60.

The container 64 and the circular tracks 68 and 68' may be fabricated from a ceramic material or non-magnetic metal because the magnetic position sensor 146 may be sensitive to surrounding metallic objects. Examples of commercially available magnetic position sensor systems, which use wound coil magnetic sensors, are the Polhemus system and the Ascension system.

Solid state phased-array transducers such as those described herein image in a plane containing the azimuthal direction of the array. More specifically, as shown in FIG. 2, the device shown would image the plane that includes the line 148 and the axis 48 at the particular rotational position shown. By rotating the acoustic device 40, as previously described, the plane being imaged would be rotated also. The mechanical stability provided by the carrier band 120 and container 64 to the flex interconnect traces 82 and electrically conductive traces 84, as described herein, allows the acoustic device 40 to undergo rapid acceleration and deceleration without buckling, jamming, binding, fatigue and unwanted vibrations. In particular, the first preferred arrangement, wherein the carrier band 120 is laminated to the flexible assembly 42 and the circular track 68 drives rotation, places little or no loading or contact on the flex interconnect traces 82 despite rapid motion of the acoustic device 40.

Figure 18:
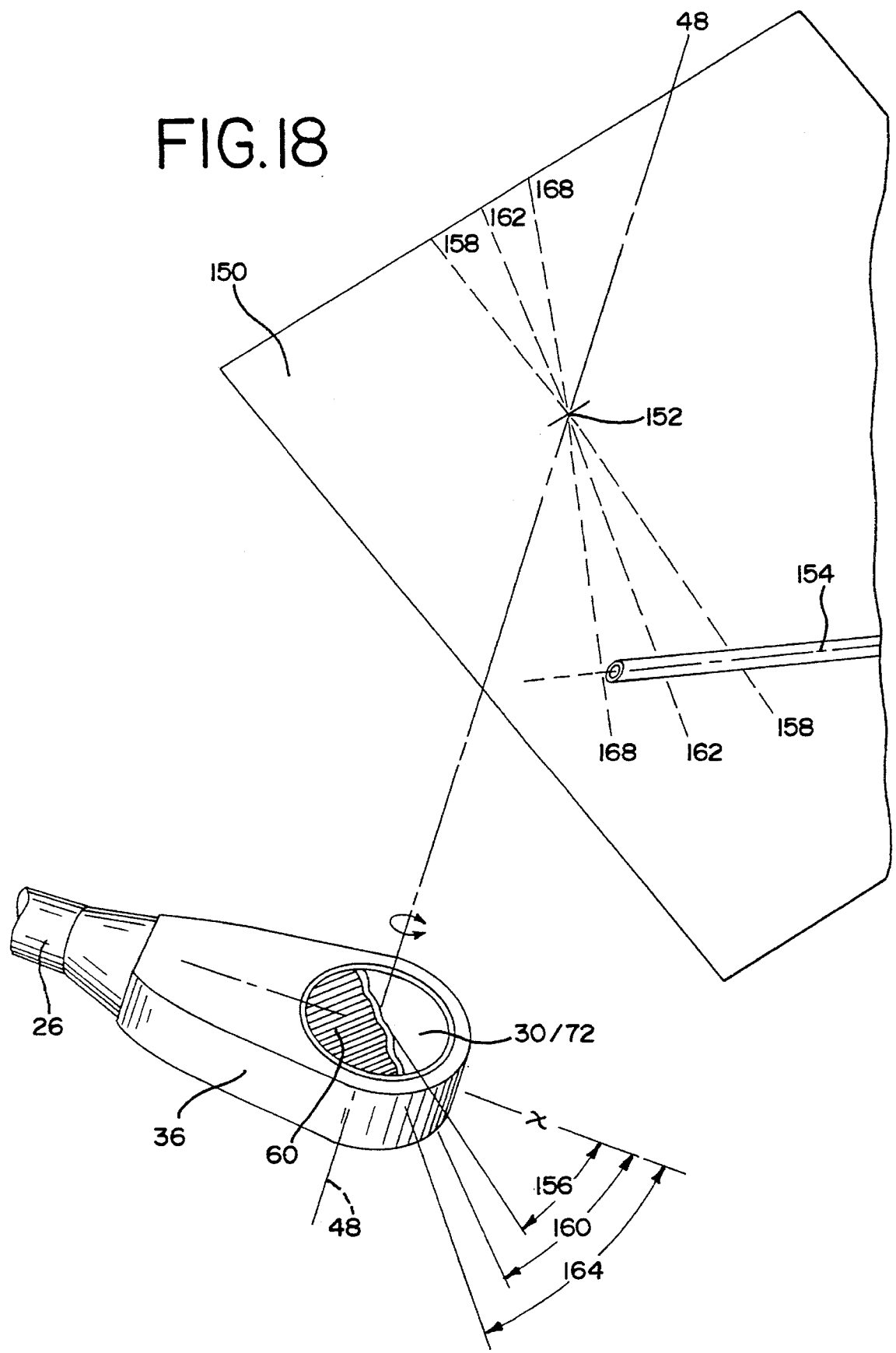
FIG. 18 is a perspective view of a compact rotationally steerable medical ultrasound transducer probe scanhead and an oblique image plane that is scanned according to a presently preferred method.

Because the acoustic device 40, flexible assembly 42 and carrier band 120 are capable of rapid acceleration and deceleration, the remotely rotationally steerable ultrasound transducer described herein is capable of selectively and directly imaging an oblique plane. Such an oblique image plane may be intersected by the axis 48 but would not contain the axis 48, as shown in FIG. 18. FIG. 18 shows, in perspective view, an oblique image plane 150 above the scanhead housing 36 of a rotationally steerable ultrasound transducer as described herein. The axis 48 through the center of the multielement transducer 60 is shown intersecting the oblique image plane 150 at a point 152. A biopsy needle 154 to be imaged is illustrated in the oblique image plane 150.

To image the oblique plane 150 the multielement transducer 60 is rotated or stepped in predetermined increments about the axis 48 over a 180 degree range, after which the rotation is reversed and the multielement transducer 60 is rotated or stepped 180 degrees in the opposite direction. A selected line in the oblique image plane 150 may be scanned at each angular position of the multielement transducer 60.

By repeating this back and forth rotation or stepping of the multielement transducer 60, sequential images of the oblique plane 150 may be produced. Alternatively, the multielement transducer 60 may be rotated back and forth through a range of less than 180 degrees to scan only a portion of the oblique image plane 150. The back and forth rotation or stepping of the multielement transducer 60 is referred to herein as slewing. The frame rate of the oblique imaging is ideally limited only by the time required for the transmitted ultrasound waves to return to the multielement transducer 60.

Referring to FIG. 18, when the rotating multielement transducer 60 is at an angle 156, a scan line 158 on the oblique plane 150 is imaged. As the transducer is rotated or stepped to an angle 160, a scan line 162 is imaged and, similarly, as the multielement transducer 60 is rotated or stepped to an angle 164, a scan line 168 is imaged. The ultrasound system (not shown) compiles image data from each of the selected scan lines, such as lines 158, 162 and 168, and provides the image data to an operator viewable display. The image data may be simultaneously or alternatively provided to a recording device (not shown).

The ultrasound system may provide the image data to the display in one of several modes, including conventional grey scale, color doppler or dual grey scale and color doppler formats. The ultrasound system would be programmed to recognize the location of the needle 154 in three dimensions, to determine the oblique plane's location, and to continuously provide updated oblique plane images for the near real-time imaging of the biopsy needle 154 or other object of interest. Oblique plane images may be interleaved with images obtained in other imaging modalities.

It will be obvious to one skilled in the art of sonography that the method of imaging an oblique plane, as described with respect to FIG. 18, may be coupled with recently introduced software-based border and edge detection methods. For example, using the method and device described herein one may in real time, or near real time, obtain oblique sectional views of an organ or artery and perform edge detection and border enhancement on them without having to do any image reconstruction on a work station, as would be required if all the image planes were coaxial with the rotational axis 48 and none of them were desirably oriented.

In this manner the remotely rotational steerable ultrasound transducer described herein may be used to form a near real-time ultrasonic image of an object in a plane that is oblique to the plane containing the axis 48 of rotation for the rotatable ultrasonic multielement transducer 60. One or more oblique image planes, such as oblique image plane 150, may be simultaneously obtained by slewing the ultrasonic multielement transducer 60 while scanning only those scan lines, such as 158, 162 and 168, making up the oblique planes of interest. Image data is sequentially extracted for sets of scan lines, such as lines 158, 162 and 168 contained in the oblique plane 150, from each plane scanned by the slewing ultrasonic multielement transducer 60. The data extraction is performed by the ultrasound system 32 software. The extracted image data may then be displayed in any desired manner, including display as an oblique slice.

Extremely rapid acceleration and deceleration of the multielement transducer 60 will be limited by the mechanical inertia and natural vibration of the flexible assembly 42 and the carrier band 120. Thus, for applications in which the multielement transducer 60 is very rapidly accelerated, an alternative arrangement of the flexible assembly 42/carrier band 120 interface with the container 64 is shown in FIGS. 19 and 20.

Figure 19:
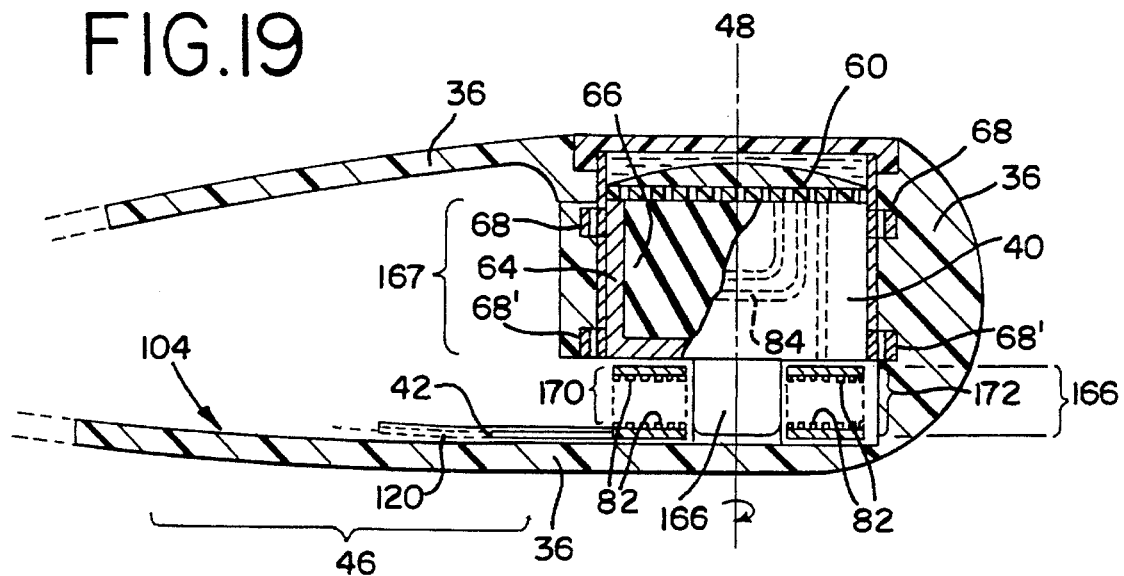
FIG. 19 is a sectional view of the probe scanhead according to a presently preferred embodiment wherein the flexible assembly forms two rolling loop regions.
Figure 20:
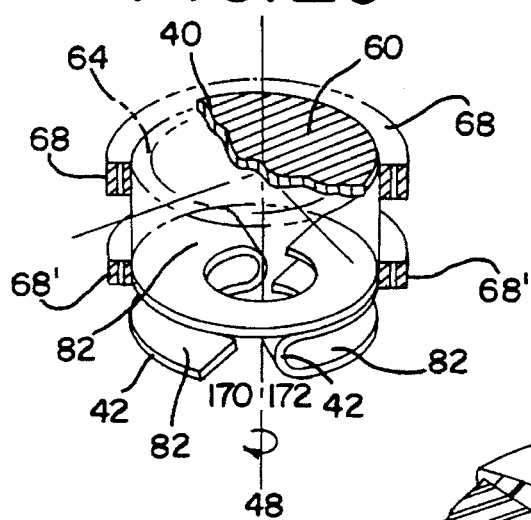
FIG. 20 is a cutaway perspective view of the acoustic device and the rolling loop regions of FIG. 19.

FIG. 19 shows an acoustic device 40 having a multielement transducer 60 and two circular tracks 68 and 68', which are centered about the axis 48. The multielement transducer 60 is rotated by at least one of the circular tracks 68 and 68' as described above with reference to the first and second preferred arrangements.

The container 64 has been modified to include an integral bottom portion 166, which has a smaller diameter than a top portion 167. By using an attenuative backing material 66 having the property of providing greater attenuation than the material 66 as shown in FIG. 12, the shorter top portion 167 can be utilized so that the low profile of the scanhead housing 36 is maintained. Highly attenuative yet nonrigid attenuative backing materials 66 may be beneficially used because of the support provided by the container 64.

In the embodiment of FIG. 19, the flexible assembly 42 and colaminated or nonlaminated carrier band 120 are attached to the surface 104 of the scanhead housing 36 in the region 46. Two rolling loop regions 170, 172 are formed by the flexible assembly 42/carrier band 120 beneath the top portion 167 of the container 64 adjacent to the integral bottom portion 166. As discussed above, the flexible assembly 42 contains flex interconnect traces 82. Electrically conductive traces 84 are fabricated upon or within the top portion 167 of the container 64. The traces 84 preferably extend along the bottom surface of the top portion 167 of the container 64 so that they may easily be connected to the flex interconnect traces 82 of the rollable flexible assembly 42. The rolling loop regions 170, 172 of the flexible assembly 42/carrier band 120 lay flat adjacent to the bottom of the top portion 167 of the container 64.

Because of the tight bending or rolling radii experienced by the flexible assembly 42 in FIGS. 19 and 20, the interconnect traces 82 may alternatively be fine gauge coaxial controlled-impedance wires, or multistrand or single strand noncoaxial wires. The wires are bound to a dielectric insulating layer, such as KAPTON™, to form the flexible assembly 42. The dielectric layer may have a surface metalization on its opposite side to serve as an electrical ground reference. By laminating the carrier band 120 to the flexible assembly 42, the carrier band 120 may alternatively serve as the electrical ground reference. Because drawn wires are more ductile and have greater fatigue resistance than deposited and etched metal films, flex interconnect traces 82 fabricated from the wires are capable of reliably enduring tighter bending or rolling radii.

FIG. 20 is a cut-away perspective view of the rolling loop regions 170, 172 below the acoustic device 40. The rolling loop regions 170, 172 roll around a circular path in opposed positions as the acoustic device 40 rotates so that the rolling loop regions 170, 172 do not interfere with each other. Because the rolling action axis of the rolling loop regions 170, 172 changes angular orientation as the acoustic device 40 rotates, the carrier band 120 colaminated to the flexible assembly 42 may further improve fatigue life.

Figure 20A:
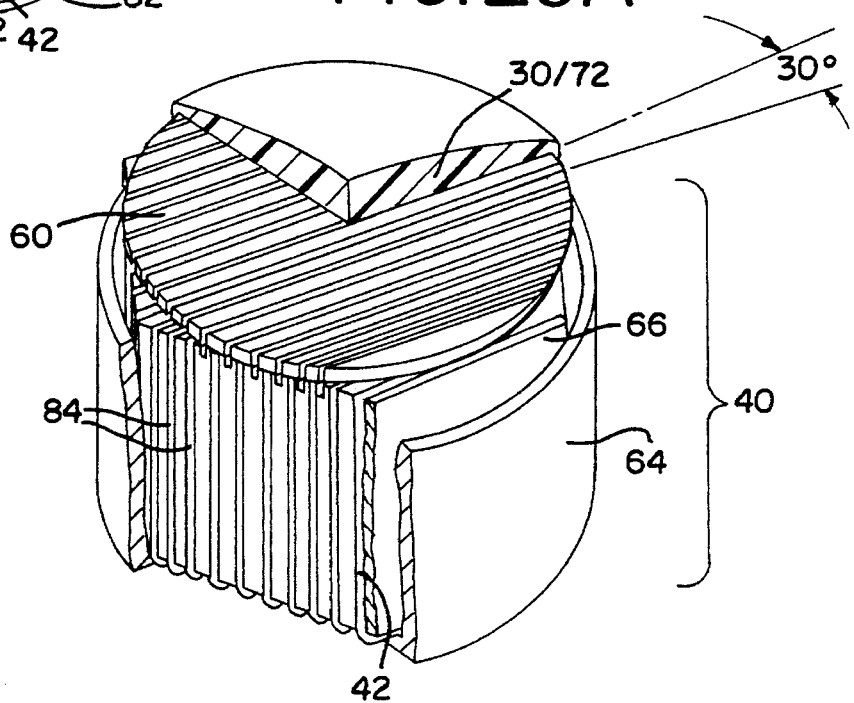
FIG. 20A is a cutaway perspective view of an alternative construction of the acoustic device shown in FIGS. 19 and 20.

In FIG. 20A, an alternative construction of the acoustic device 40 is provided that allows a direct connection between the flexible assembly 42, which may form the rolling loop regions 170, 172, and the multielement transducer 60. The attenuative backing material 66 is approximately hexagonal in shape. A first flexible assembly 42 is bonded to the top of the attenuative backing material 66 with the flex interconnect traces 82 facing upward. The first flexible assembly 42 is then folded over one of the flat faces of the hexagonal attenuative backing material 66. An additional fold at the bottom of the flat face may allow the flexible assembly 42 to be routed beneath the acoustic device 40 where an integral rolling deformable loop, such as 170 in FIGS. 19 and 20, may be formed. A second flexible assembly 42' (not shown) is bonded to the top of the attenuative backing material 66 directly opposite to the first flexible assembly 42 and is folded over the opposite flat face of the hexagonal material 66. The second flexible assembly 42' may also be routed beneath the acoustic device 40, where an integral rolling deformable loop, such as 172 in FIGS. 19 and 20, may be formed. The multielement transducer 60 is bonded to the top of the first and second flexible assemblies 42, 42'. The container 64 surrounds the hexagonal faces of the attenuative backing material 66, which have the flexible assemblies 42, 42' bonded thereto.

An asymmetrical arrangement of the hexagonal attenuative backing material 66, in which the flat faces of the material 66 are of slightly differing widths so that the individual acoustic elements 130 of the multielement transducer 60 are oriented at 30 degrees to the hexagonal face of the material 66 that contains the mating flex interconnect traces 84, is preferred. By using the 30 degree orientation, the individual acoustic elements 130 in one half of the multielement transducer 60 will intersect one face of the hexagonal attenuative backing material 66, and the remaining half of the individual acoustic elements 130 will intersect the opposite face of the hexagonal attenuative backing material 66. Thus, one half of the multielement transducer 60 may be coupled to the flexible assembly 42, and the remaining half may be coupled to the flexible assembly 42'. By having each half of the multielement transducer routed to a dedicated and separate flexible assembly, electrical crosstalk between the flex interconnect traces 82 can be substantially avoided. This is particularly the case when the multielement transducer 60 is operated in the continuous wave doppler mode, wherein one half of the multielement transducer 60 transmits while the remaining half receives.

Figure 22:
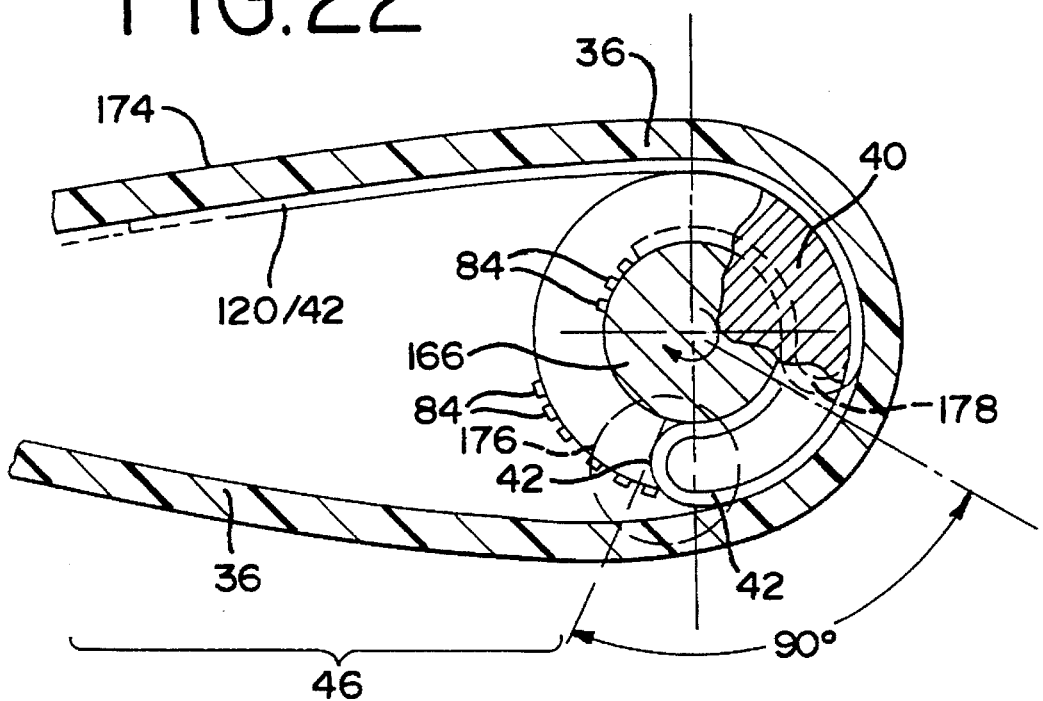
FIG. 22 is a top sectional view of the scanhead probe shown in FIG. 21.
Figure 21:
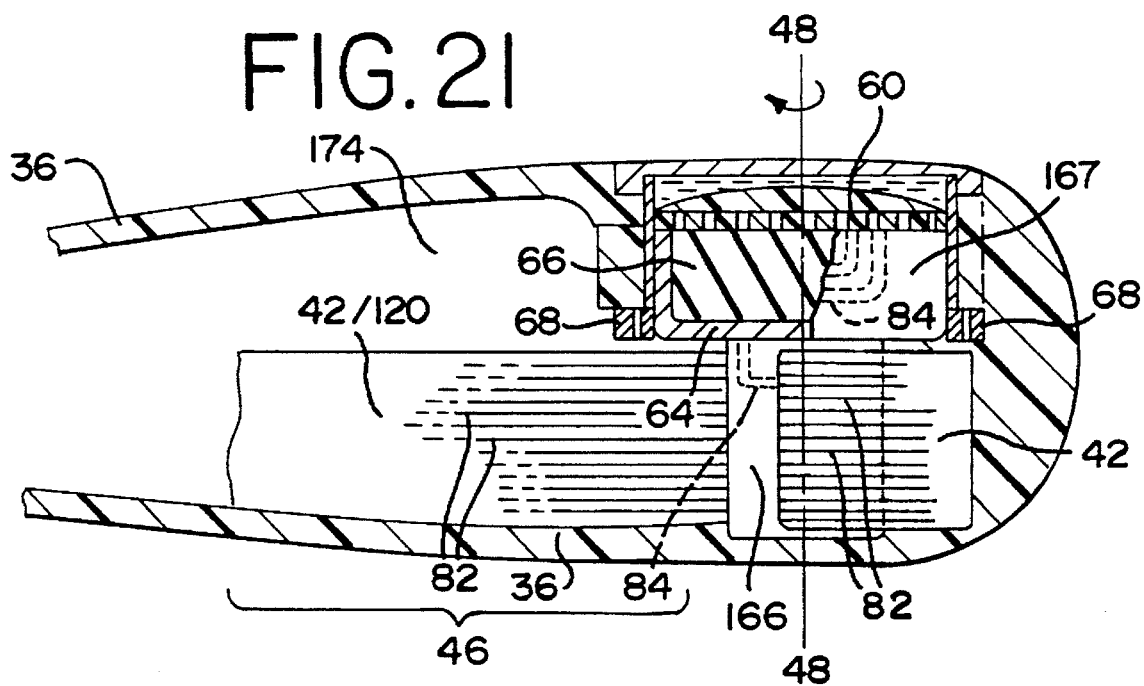
FIG. 21 is a sectional view of the scanhead probe showing an alternative arrangement of the flexible assembly shown in FIG. 19.

FIGS. 21 and 22 show an alternative embodiment of the rotationally steerable transducer shown in FIGS. 19 and 20. In this embodiment, the acoustic device 40 is driven in rotation about the axis 48 by the circular track 68 as described with respect to the first and second preferred arrangements. As shown in FIG. 21, the flexible assembly 42 is attached to the side wall 174 of the scanhead housing 36. The flexible assembly 42 is connected to the integral bottom portion 166 of the container 64. The electrically conductive traces 84 are routed, via top portion 167, from the multielement transducer 60 onto or into the bottom portion 166. The flex interconnect traces 82 from the flexible assembly 42 are connected to the mating electrically conductive traces 84.

As shown in FIG. 22, a rolling loop region 176 is formed at the end of the flexible assembly 42 beneath the acoustic device 40. As the acoustic device 40 rotates, the rolling loop region 176 rolls beneath the acoustic device 40. The phantom outline 178 of the flexible assembly 42 shows the position of the flexible assembly 42 after the acoustic device 40 is rotated counter-clockwise approximately 90 degrees. As discussed with respect to FIG. 20, the fatigue life of the apparatus may be improved by utilizing the carrier band 120 colaminated to the flexible assembly 42 as described with respect to the first preferred arrangement.

There is no movable portion of the flexible assembly 42 in the region 46 in the embodiments shown in FIGS. 19 through 22. The flexible assembly 42 and the carrier band 120 are fixed to the scanhead housing 36 in the region 46, and one or both of the circular tracks 68 and 68' drive rotation of the acoustic device 40 as well as provide rotational guidance to the acoustic device 40. Accordingly, the region 46 may be used for other functions or may be reduced in dimension to reduce the overall size of the scanhead housing 36. Further, because the carrier band 120 does not drive the rotation of the acoustic device 40 and the flexible assembly 42 is attached to the scanhead housing 36, in the embodiments shown in FIGS. 19 through 22, the carrier band 120 is not mechanically necessary to prevent buckling, jamming and abrasion of the flexible assembly 42 except as such events may be caused by the rolling action. The carrier band 120 may, therefore, be omitted or, alternatively, utilized for electrical and/or thermal purposes as described above.

It is intended that the foregoing detailed description be regarded as illustrative rather than limiting and that it is understood that the following claims including all equivalents are intended to define the scope of the invention.

We claim:

1. An ultrasonic probe for use with a remote ultrasonic imaging system comprising:

a multielement transducer having an upper surface and a lower surface;

a substantially uninterrupted ultrasonically attenuative backing material adjacent to the lower surface of the multielement transducer;

a container having a wall and a bottom, the attenuative backing material being disposed within the container;

a track connected to the container, wherein the track positions the container for rotation about an axis;

a flexible assembly attached to the container; and a carrier band having a distal end that is attached to the container, the carrier band operable to rotate the container about the axis defined by the track.

2. The ultrasonic probe of claim 1 wherein the track is circular.

3. The ultrasonic probe of claim 2, further comprising a scanhead housing for housing the multielement transducer and the container wherein a torsional spring is attached to the container and the scanhead housing.

4. The ultrasonic probe of claim 3 wherein the circular track further comprises:

an inner rotating ring attached to and encircling the container;

an outer stationary ring attached to the scanhead housing, the outer stationary ring positioned concentrically with the inner rotating ring; and a plurality of ball bearings located between the inner rotating ring and the outer stationary ring, the ball bearings making continuous contact with the inner rotating ring and the outer stationary ring.

5. The ultrasonic probe of claim 3 wherein the circular track further comprises:

a rotating ring attached to the bottom of the container;

a stationary ring attached to the scanhead housing below the rotating ring, the stationary ring positioned concentrically with the rotating ring; and a plurality of ball bearings located between the rotating ring and the stationary ring, the ball bearings making continuous contact with the rotating ring and the stationary ring.

6. The ultrasonic probe of claim 3 wherein the circular track further comprises:

an inner rotating ring attached to and encircling the container;

an outer stationary ring attached to the scanhead housing, the outer stationary ring positioned concentrically with the inner rotating ring; and a lubricating layer located between the inner rotating ring and the outer stationary ring, wherein the lubricating layer facilitates relative motion between the inner ring and the outer ring.

7. The ultrasonic probe of claim 3 wherein the circular track further comprises:

a rotating ring attached to the bottom of the container;

a stationary ring attached to the scanhead housing below the rotating ring, the stationary ring positioned concentrically with the rotating ring; and a lubricating layer located between the rotating ring and the stationary ring, wherein the lubricating layer facilitates relative motion between the rotating ring and the stationary ring.

8. The ultrasonic probe of claim 3 wherein the circular track further comprises a band slidably mounted in a circular groove formed in the scanhead housing below the container, the container being mounted on the band.

9. An ultrasonic probe as claimed in claim 2 further comprising a magnetic position sensor rigidly attached to the container.

10. The ultrasonic probe of claim 9 wherein the container and the circular track are fabricated of ceramic material.

11. An ultrasonic probe as claimed in claim 2 further comprising a second circular track attached to the container.

12. The ultrasonic probe of claim 1 wherein the container further comprises a cylindrical wall and a circular bottom.

13. The ultrasonic probe of claim 12 wherein the flexible assembly and the distal end of the carrier band are attached to the cylindrical wall of the container such that as the container rotates the flexible assembly is disposed between the container and the carrier band.

14. The ultrasonic probe of claim 1 further comprising:

a plurality of electrically conductive traces formed on an outer surface of the wall of the container; and a plurality of flex interconnect traces carried by the flexible assembly, the plurality of flex interconnect traces being coupled to the plurality of electrically conductive traces.

15. The ultrasonic probe of claim 14 wherein the plurality of flex interconnect traces carried by the flexible assembly are coupled to the plurality of electrically conductive traces at a location on the outer surface of the wall of the container and the carrier band is attached at a second location on the outer surface of the wall of the container such that the flexible assembly is disposed between the carrier band and the wall of the container.

16. The ultrasonic probe of claim 15 wherein the carrier band is operable to conduct heat away from the container.

17. The ultrasonic probe of claim 14 wherein the plurality of electrically conductive traces are coupled to the upper surface of the multielement transducer.

18. The ultrasonic probe of claim 17 wherein the multielement transducer comprises a plurality of electrically independent elements each having an upper surface and a lower surface, the upper surface of each of the plurality of electrically independent elements coupled to one of the plurality of electrically conductive traces.

19. The ultrasonic probe of claim 18 wherein the upper surface of the plurality of electrically independent elements is flush with the wall of the container.

20. The ultrasonic probe of claim 19 further comprising at least one electrically conductive ground electrode coupled to the lower surface of the plurality of electrically independent elements and disposed between the container and the acoustically attenuative material.

21. The ultrasonic probe of claim 14 wherein the plurality of electrically conductive traces are coupled to the lower surface of the multielement transducer array.

22. The ultrasonic probe of claim 21 wherein the multielement transducer comprises a plurality of electrically independent elements each having an upper surface and a lower surface, the lower surface of each of the plurality of electrically independent elements coupled to one of the plurality of electrically conductive traces.

23. The ultrasonic probe of claim 22 wherein the lower surface of each of the plurality of electrically independent elements is attached to a top surface of the wall of the container.

24. The ultrasonic probe of claim 1 further comprising a control wire connected to a proximal end of the carrier band, the control wire passing through a guidetube in a gastroscope to a control housing.

25. The ultrasonic probe of claim 24 wherein a linear piezomotor is positioned in the control housing and connected to the control wire, the linear piezomotor operable to exert a driving force upon the control wire to rotate the container.

26. The ultrasonic probe of claim 24 wherein a linear actuator is positioned in the control housing and connected to the control wire, the linear actuator operable to exert a driving force upon the control wire to rotate the container.

27. An ultrasonic probe as claimed in claim 1 wherein the container has a top portion and a bottom portion, the bottom portion having a smaller diameter than the top portion, the carrier band being attached to the bottom portion of the container.

28. An ultrasonic probe comprising:

a multielement transducer having an upper surface and a lower surface;

a support structure attached to the multielement transducer;

a gear ring attached to the support structure;

a scanhead housing for housing the multielement transducer and the support structure;

a mechanism mounted to a surface of the scanhead housing and positioned to engage the ring;

a cable coupled to the mechanism and operable to rotate the support structure about an axis defined by the ring;

a flexible assembly coupled to the multielement transducer; and a carrier band having a distal end that is attached to the support structure.

29. The ultrasonic probe of claim 28 wherein the mechanism is a spur gear.

30. The ultrasonic probe of claim 28 wherein the mechanism is a bevel gear.

31. The ultrasonic probe of claim 28 wherein the mechanism is a hypoid gear.

32. An ultrasonic probe for use with a remote ultrasound imaging system comprising:

a multielement transducer having an upper surface and a lower surface;

an ultrasonically attenuative material adjoining the lower surface of the multielement transducer;

a container supporting the ultrasonically attenuative material;

a scanhead housing for housing the multielement transducer and the container;

a rotor ring attached to the container;

a stator ring position below the rotor ring and attached to the scanhead housing, whereby the stator ring and the rotor ring form a piezomotor operable to rotate the container;

a flexible assembly attached to the container; and a carrier band attached to the container.

33. The ultrasonic probe of claim 32 further comprising:

a plurality of electrically conductive traces formed on an outer surface of a wall of the container; and a plurality of flex interconnect traces carried by the flexible assembly, the plurality of flex interconnect traces being coupled to the plurality of electrically conductive traces.

34. The ultrasonic probe of claim 23 wherein the plurality of electrically conductive traces are coupled to the upper surface of the multielement transducer.

35. The ultrasonic probe of claim 34 wherein the multielement transducer comprises a plurality of electrically independent elements each having an upper surface and a lower surface, the upper surface of each of the plurality of electrically independent elements coupled to one of the plurality of electrically conductive traces.

36. The ultrasonic probe of claim 32 wherein the carrier band is attached to the flexible assembly and the flexible assembly is positioned between the container and the carrier band, the carrier band being operable to conduct heat away from the container.

37. In an ultrasonic imaging system having a multielement ultrasonic transducer, a probe for housing and manipulating the multielement ultrasonic transducer, and signal processing circuitry for generating and receiving electrical signals representative of acoustic signals transmitted and received by the transducer, apparatus for electrically connecting the transducer to the signal processing circuitry and manipulating the transducer comprising:

container means associated with the probe for supporting the transducer, the container means having an external surface;

track means connected with the container means for mounting and guiding the container means for rotation about an axis;

carrier means connected to the external surface of the container means and remotely manipulatable for rotating the container means about the axis; and flexible circuit means for electrically connecting each of the elements of the transducer to the signal processing circuitry.

38. The apparatus of claim 37 wherein an ultrasonically attenuative backing means is disposed within the container means adjacent one surface of the transducer.

39. The apparatus of claim 38 wherein the carrier means and the flexible circuit means are cowrapped around the container means, the flexible circuit means positioned between the container means and the carrier means.

40. The apparatus of claim 37 wherein the track means comprises:

an inner rotating ring attached to and encircling the container means;

an outer stationary ring attached to a scanhead housing for housing the transducer and container means, the outer stationary ring positioned concentrically with the inner rotating ring; and a plurality of ball bearings located between the inner rotating ring and the outer stationary ring, the ball bearings making continuous contact with the inner rotating ring and the outer stationary ring.

41. The apparatus of claim 37 wherein the track means comprises:

a rotating ring attached to the bottom of the container means;

a stationary ring attached to a scanhead housing for housing the transducer and container means below the rotating ring, the stationary ring positioned concentrically with the rotating ring; and a plurality of ball bearings located between the rotating ring and the stationary ring, the ball bearings making continuous contact with the rotating ring and the stationary ring.

42. The apparatus of claim 37 wherein the track means comprises:

an inner rotating ring attached to and encircling the container means;

an outer stationary ring attached to a scanhead housing for housing the transducer and container means, the outer stationary ring positioned concentrically with the inner rotating ring; and a lubricating layer located between the inner rotating ring and the outer stationary ring, wherein the lubricating layer facilitates relative motion between the inner ring and the outer ring.

43. The apparatus of claim 37 wherein the track means comprises:

a rotating ring attached to a bottom of the container means;

a stationary ring attached to a surface of the scanhead housing below the rotating ring, the stationary ring positioned concentrically with the rotating ring; and a lubricating layer located between the rotating ring and the stationary ring, wherein the lubricating layer facilitates relative motion between the rotating ring and the stationary ring.

44. In an ultrasonic imaging system having a multielement ultrasonic transducer, a probe for housing and manipulating the multielement ultrasonic transducer and signal processing circuitry for generating and receiving electrical signals representative of acoustic signals transmitted and received by the transducer, apparatus for simultaneously electrically connecting the transducer to the signal processing circuitry and manipulating the transducer comprising:

container means associated with the probe for housing the transducer;

track means connected with the container means for mounting the container means for rotation about an axis and remotely manipulatable for rotating the container means about the axis;

carrier means having a distal end that is connected to an external surface of the container means; and flexible circuit means for electrically connecting each of the elements of the transducer to the signal processing circuitry.

45. The apparatus of claim 44 wherein the multielement transducer comprises a plurality of piezoelements curved in an elevation direction to provide elevational focusing.

46. The apparatus of claim 44 wherein the track means comprises:

at least one recess formed in a bottom of the container means; and a band slidably mounted in a circular groove formed on an internal surface of the probe below the container means, the band having at least one peg attached thereto such that the peg projects into the recess in the bottom of the container means.

47. The apparatus of claim 46 further comprising two control cables, each control cable being connected to an opposite end of the band.

48. The apparatus of claim 46 further comprising a control cable attached to an end of the band, and a torsional spring connected between the probe and the container means.

49. The apparatus of claim 44, further comprising means for sensing a position of the multielement ultrasonic transducer, wherein said sensing means is fixed to said container means.

50. The apparatus of claim 49, wherein the carrier means is laminated to the flexible circuit means.

51. A compact rotationally steerable ultrasound transducer for use with a remote ultrasonic imaging system and a gastroscope, comprising:

a tubular container having two open ends;

an ultrasonically attenuative backing material disposed within the tubular container;

a first multielement transducer having an upper surface and a lower surface, the first array being attached to one open end of the tubular container so that the lower surface adjoins the attenuative backing material;

a second multielement transducer having an upper surface and a lower surface, the second array being attached to the second open end of the tubular container so that the lower surface adjoins the attenuative backing material;

a scanhead housing for housing the first and second multielement transducers and the container;

at least one circular track encircling the tubular container and being fixed to the scanhead housing;

a flexible assembly attached to the container; and a carrier band attached to the container, the carrier band positioned between the flexible assembly and the scanhead housing.

52. A compact rotationally steerable ultrasound transducer as claimed in claim 51, wherein the carrier band is operable to rotate the container about an axis defined by the circular track.

53. A compact rotationally steerable ultrasound transducer as claimed in claim 51, wherein at least one circular track is operable to rotate the container about an axis defined by the circular track.

54. The transducer of claim 51 further comprising:

a plurality of electrically conductive traces formed on an outer surface of a wall of the tubular container; and a plurality of flex interconnect traces carried by the flexible assembly, the plurality of flex interconnect traces being coupled to the plurality of electrically conductive traces.

55. The transducer of claim 54 wherein a number of the plurality of electrically conductive traces is coupled to the upper surface of the first multielement transducer, and a number of the plurality of electrically conductive traces is coupled to the upper surface of the second multielement transducer.

56. The transducer of claim 55 wherein the first multielement transducer and the second multielement transducer comprise a plurality of electrically independent elements each having an upper surface and a lower surface, the upper surface of each of the plurality of electrically independent elements coupled to one of the plurality of electrically conductive traces.

57. A compact rotationally steerable ultrasound transducer for use with a remote ultrasonic imaging system and a gastroscope, comprising:

a multielement transducer having an upper surface and a lower surface;

a substantially uninterrupted ultrasonically attenuative backing material adjacent to the lower surface of the multielement transducer;

a container having an internal surface and an external surface, the attenuative backing material being disposed within the container adjacent to the internal surface;

a flexible assembly having at least two layers wherein one of the layers is a carrier band, at least one of the layers of the flexible assembly being connected to the container; and a circular track mounted to the external surface of the container, the circular track operable to rotate the multielement transducer.

58. The compact rotationally steerable ultrasound transducer of claim 57 wherein the carrier band is a common electrical ground return for the multielement transducer.

59. The compact rotationally steerable ultrasound transducer of claim 57 wherein the carrier band is an electrical ground plane for the flexible assembly.

60. The compact rotationally steerable ultrasound transducer of claim 57 wherein the carrier band is attached to the container, the carrier band being thermally conductive, whereby the carrier band conducts heat away from the container.

61. The transducer of claim 57 wherein another one of the at least two layers comprises a plurality of flex interconnect traces.

62. The transducer of claim 61 wherein the plurality of flex interconnect traces are positioned between the carrier band layer and the container.

63. A compact rotationally steerable ultrasound transducer as claimed in claim 57 wherein one of the at least two layers comprises a plurality of wires.

64. A compact rotationally steerable ultrasound transducer as claimed in claim 63 wherein the plurality of wires are multistrand noncoaxial wires.

65. A compact rotationally steerable ultrasound transducer for use with a remote ultrasonic imaging system and a gastroscope, comprising:

a container disposed within a scanhead housing, the container having a top portion disposed upon a bottom portion wherein the bottom portion extends below the top portion;

a circular track encircling and attached to the top portion of the container, the circular track supported by the scanhead housing, defining an axis of rotation and operable to rotate the container about the axis;

an ultrasonically attenuative backer material disposed within the top portion of the container;

a multielement transducer having an upper surface and a lower surface, the lower surface adjoining the attenuative backer material; and a first flexible assembly coupled to the multielement transducer.

66. The compact rotationally steerable ultrasound transducer of claim 65 wherein the first flexible assembly is connected to the bottom portion of the container, the flexible assembly forming a rolling loop region below the top portion of the container.

67. The compact rotationally steerable ultrasound transducer of claim 65 further comprising a second flexible assembly coupled to the multielement transducer, the first and second flexible assemblies forming rolling loop regions below the top portion of the container.

68. The transducer of claim 65 wherein the flexible assembly comprises at least two layers of which one of the layers is a carrier band.

69. The transducer of claim 68 wherein another one of the at least two layers of the flexible assembly comprises a plurality of flex interconnect traces.

70. The transducer of claim 69 wherein the plurality of flex interconnect traces are coupled to a plurality of electrically conductive traces located on the bottom portion of the container.

71. The transducer of claim 70 wherein the multielement transducer comprises a plurality of electrically independent elements, the plurality of electrically independent elements being coupled to the plurality of electrically conductive traces.

72. A compact rotationally steerable ultrasound transducer as claimed in claim 70, wherein the flexible assembly forms a rolling loop region below the top portion of the container, the rolling loop region having a vertical axis of rolling action.

73. The transducer of claim 69 wherein the plurality of flex interconnect traces are coupled to a plurality of electrically conductive traces located on a bottom of the top portion of the container.

74. The transducer of claim 73 wherein the multielement transducer comprises a plurality of electrically independent elements, the plurality of electrically independent elements being coupled to the plurality of electrically conductive traces.

75. A compact rotationally steerable ultrasound transducer as claimed in claim 73, wherein the flexible assembly forms a rolling loop region below the top portion of the container, the rolling loop region having a horizontal axis of rolling action.

76. A compact rotationally steerable ultrasound transducer as claimed in claim 65, wherein the attenuative backer material has a top, a bottom, and six sides such that the material is hexagonal in shape.

77. A compact rotationally steerable ultrasound transducer as claimed in claim 76, further comprising a second flexible assembly coupled to the multielement transducer, the first and second flexible assemblies bonded to opposite sides of the hexagonal attenuative backer material.

78. A compact rotationally steerable ultrasound transducer as claimed in claim 77, wherein the first and second flexible assemblies extend through a bottom of the top portion of the container, each of the flexible assemblies forming a rolling loop region below the top portion of the container.

79. In an ultrasonic imaging system that includes a probe for housing and manipulating a multielement ultrasonic transducer and signal processing circuitry for generating and receiving electrical signals representative of acoustic signals transmitted and received by said transducer, apparatus for transmitting and receiving ultrasonic signals and simultaneously electrically connecting said transducer to said signal processing circuitry and manipulating said transducer comprising:

an array of piezoelements, the piezoelements curved in an elevation direction;

a container for supporting the curved array;

a track connected to the container for mounting the container for rotation about an axis;

a flexible assembly for electrically connecting each of the piezoelements of the curved array to the signal processing circuitry; and a carrier band connected to the container and remotely manipulatable for rotating the container about the axis.

80. An ultrasonic probe for use with a remote ultrasonic imaging system comprising:

transducer means for transmitting and receiving ultrasonic signals;

attenuative means for absorbing ultrasonic signals;

container means for supporting the attenuative means, wherein the attenuative means forms a substantially uninterrupted backing below the transducer means;

track means connected to the container means for mounting and guiding the container means for rotation about an axis;

flexible circuit means for electrically connecting the transducer means to the remote ultrasonic imaging system; and carrier means connected to the container means for rotating the container means about the axis defined by the track means.

81. A method of forming a near real-time ultrasonic image of at least a portion of a surface, comprising:

slewing an ultrasonic multielement transducer about an axis of rotation to a plurality of angular positions;

scanning, at each angular position., a selected scan line within a surface intersecting the axis in at most one point; and displaying the selected scan line scanned at each angular position, the displayed scan lines forming the image of the surface.

82. The method of claim 81 further comprising providing the selected scan line scanned at each angular position to a recording device.

83. The method of claim 81 wherein the surface is a plane.

84. The method of claim 83 wherein a plurality of planes are simultaneously scanned.

85. The method of claim 81 wherein the selected scan lines are displayed in a color doppler imaging mode.

86. An ultrasonic probe for use with a remote ultrasonic imaging system comprising:

a scanhead disposed at a distal end of the probe, the scanhead having an internal surface upon which a groove is formed;

a support structure disposed within the scanhead adjacent to the groove;

a multielement transducer mounted to the support structure;

a band slidably disposed within the groove;

driving means coupled to the band; and at least one member located to engage the support structure, wherein the at least one member fixes the relative position between the band and the support structure.

87. An ultrasonic probe as claimed in claim 86, wherein the groove has a circular region, whereby a portion of the sliding band moves in a circular motion, and the support structure rests directly on the portion of the band.

88. An ultrasonic probe as claimed in claim 86, wherein the at least one member attached to the band comprises a pin that is attached to the sliding band, and wherein the support structure is fabricated with a recess that mates with the pin.

89. An ultrasonic probe as claimed in claim 88, wherein the support structure rests on the internal surface of the scanhead and a plurality of pins attached to the band project from the groove into a plurality of corresponding recesses in the support structure.

90. An ultrasonic probe as claimed in claim 86, further comprising means for lubricating the groove.

91. An ultrasonic probe as claimed in claim 86, wherein the groove is formed from a self-lubricating material.

\* \* \* \* \*